United States Patent [19]

Saita et al.

[11] Patent Number: 5,434,292
[45] Date of Patent: Jul. 18, 1995

[54] PHENYLALKANOIC ACID DERIVATIVES, PROCESS FOR PRODUCING THE SAME AND PROCESS FOR SEPARATING OPTICAL ISOMERS THEREOF

[75] Inventors: Masaru Saita; Hisataka Inoue; Koichi Beppu; Terumi Hachiya; Ikuo Shinohara; Yasuaki Taniguchi; Yoshiki Deguchi; Yoshihiro Hamaguchi, all of Tosu, Japan

[73] Assignee: Hisamitsu Pharmaceutical Co., Inc., Tosu, Japan

[21] Appl. No.: 193,081

[22] Filed: Feb. 4, 1994

[51] Int. Cl.⁶ ................................. C07C 69/76
[52] U.S. Cl. ........................... 560/51; 560/53; 560/21; 560/57; 562/435; 562/463; 562/468
[58] Field of Search ............ 560/51, 53, 21, 57; 562/435, 463, 465; 514/530, 541, 545, 568

[56] References Cited

PUBLICATIONS

CA 100:51183 1984.
CA: 102:95400 1984.
CA 104:68603 1985.

*Primary Examiner*—Paul J. Killos
*Attorney, Agent, or Firm*—Bucknam and Archer

[57] ABSTRACT

A novel phenylalkanoic acid derivative represented by the following formula

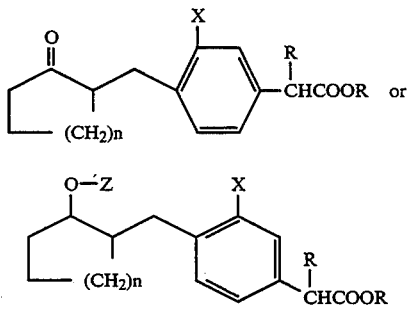

wherein n is an integer of 1-2, X is a halogen atom, alkoxyl group or nitro group, R is a hydrogen atom or alkyl group, and Z is a hydrogen atom or acyl group, a method for producing said derivative, a method for separating the optical isomers of said derivative from each other, as well as an anti-inflammatory drug, analgesic drug or preparation for external use each containing said derivative.

23 Claims, No Drawings

PHENYLALKANOIC ACID DERIVATIVES, PROCESS FOR PRODUCING THE SAME AND PROCESS FOR SEPARATING OPTICAL ISOMERS THEREOF

TECHNICAL FIELD

This invention relates to phenylalkanoic acid derivatives useful as pharmaceuticals which have excellent anti-inflammatory and analgesic actions and high safety, particularly remarkable effects on chronic inflammations. Further, it relates to a process for producing the phenylalkanoic acid derivatives in a good yield and also to a process for separating optical isomers thereof in an excellently selective manner. Furthermore, it relates to an anti-inflammatory agent, an analgesic agent and externally-used preparation which each contains said phenylalkanoic acid derivative as an effective ingredient.

BACKGROUND ART

Phenylalkanoic acid derivatives which have heretofore been known, are disclosed respectively in Japanese Patent Gazette No. Sho 58-4699 or 4699/83 (hereinafter referred to as Prior Art 1) and Japanese Pat. Appln. Laid-Open Gazette No. Sho 54-103852 or 103852/79 (hereinafter referred to as Prior Art 2).

The Prior Art 1 concretely discloses 2-[4-(2-oxocyclopentane-1-yl methyl)phenyl]propionic acid, 4-(2-oxocyclopentane-1-yl methyl)phenylacetic acid, 2-[4-(2-oxocyclohexane-1-yl methyl)phenyl]propionic acid, 4-(2-oxocyclohexane-1-yl methyl)phenylacetic acid and the like and reports that these compounds have anti-inflammatory, analgesic and anti-febrile actions.

On the other hand, the Prior Art 2 widely describes phenylacetic acid derivatives represented by the following formula (P)

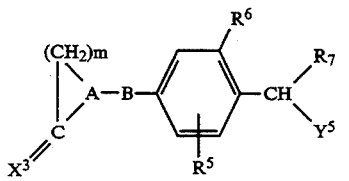
(P)

wherein m is an integer of 1–5, $>A-B-$ is $>CH-CH_2-$, $>C=CH-$ or $>CH-CO-$, $R^5$ is a hydrogen atom, halogen atom, trifluoromethyl group, nitro group or amino group, $R^6$ and $R^7$ are each a hydrogen atom or lower alkyl group or they together form an ethylene group, $X^3$ is two hydrogen atoms or oxo, and $Y^5$ is cyano, hydroxyamidocarbonyl, carbamoyl, 5-tetrazolyl, carboxyl, a salt thereof with a physiologically acceptable base, an ester thereof with a physiologically safe alcohol or an amide thereof with a physiologically safe amine.

The general formula (P) in the Prior Art 2 prima facie partly covers the phenylalkanoic acid derivatives of this invention, but the Prior Art 2 only describes concretely, as compounds similar to the derivatives of this invention, 2-(4-cyclopentylmethylphenyl)-propionic acid, 4-(cyclopentylmethyl)-phenylacetic acid, 2-(3-chloro-4-cyclopentylmethylphenyl)-propionic acid, 2-(4-cyclohexylmethylphenyl)-propionic acid, 2-(4-cyclopentylmethyl-3-nitrophenyl)-propionic acid, 2-[4-(2-oxopentylidenemethyl)-phenyl]-propionic acid, 2-(4-cyclopentylidenemethyl)-phenyl-propionic acid, and the like.

In addition, the patent application laid open in the Prior Art 2 (said Pat. Appln. Laid-Open Gazette No. Sho 54-103852) has already been published under Patent Gazette No. Hei 1-34980 or 34980/89 claiming a right to lndane-1-carboxylic acid derivatives, not to phenylalkanoic acid derivatives at all.

As mentioned above, the Prior Art 2 does not concretely disclose anything about the phenylalkanoic acid derivatives of this invention and only vaguely expresses such compounds in a higher technical concept. Thus, the Prior Arts 1 and 2 do not concretely disclose anything about the phenylalkanoic acid derivatives of this invention and, further, they do not disclose that said derivatives have remarkable analgesic and anti-inflammatory actions with very little side effects. Further, the compounds concretely disclosed in the Prior Arts 1 and 2 do not have sufficient analgesic and anti-inflammatory or antiphlogistic actions without hardly raising any problems as to their side effects.

Accordingly, the phenylalkanoic acid derivatives of this invention described later are novel compounds which have remarkable effects and have been specially selected among very many compounds expected from the general formula (P) described as a higher technical concept particularly in the Prior Art 2.

In addition, ibuprofen, loxoprofen, ketoprofen and the like have been known as non-steroid type acidic antiphlogistic agents having a phenylalkanoic acid as their partial structure. These non-steroid type compounds are appreciated to be very different in physiological profile (or properties) from each other depending on the kind of a substituent attached to the para- or meta-position of a phenylalkanoic acid.

Japanese Patent Gazette No. Hei 1-35806 or 35806/89 (hereinafter referred to as Prior Art 3) and Japanese Pat. Appln. Laid-Open Gazette No. Sho 60-78844 or 178844/85 (hereinafter referred to as Prior Art 4) report on 2-[4-(2-hydroxycyclopentane-1-yl methyl)phenyl]-propionic acid and 2-[4-(2-hydroxycyclohexyl methyl)-phenyl]propionic acid. These compounds so reported are also recognized to have large effects on physiological profile due to slight structural differences in stereocoordination. In short, these Prior Arts have found that a compound having analgesic and antiphlogistic actions can be obtained by selecting a substituent at the paraposition in a phenylalkanoic acid. These above facts substantiate that a slight change in the chemical structure of a medicine will have great effects on the physiological profile thereof, but said Prior Arts neither disclose nor even suggest anything at all about a concept that a phenylalkanoic acid is enhanced in its physiological profile by further introducing other substituents onto the benzene ring of the phenylalkanoic acid.

The aforementioned Prior Arts 3 and 4 describe stereoisomers or optical isomers, which are (2S)-2-[4-(2-hydroxycyclopentane-1-yl methyl)phenyl] propionic acid and 2-[4-(2-hydroxycyclohexyl methyl)phenyl] propionic acid. These isomeric compounds are described in said Prior Arts to have analgesic and anti-inflammatory (antiphlogistic) actions, but their efficacy is not sufficient.

Ibuprofen, flurbiprofen, loxoprofen, alminoprofen, alclofenac and the like which are known as phenylalkanoic acid-type non-steroid analgesic and anti-inflammatory drugs, will be rapidly absorbed through digestive canals when they are administered as oral drugs, thereby to exert analgesic and anti-inflammatory actions.

According to clinical reports on side effects of the above non-steroid type medicines, however, these medicines when orally taken will have side effects such as digestive canal troubles, dropsy, cutaneous troubles and sleepiness.

Further, a non-steroid acidic anti-inflammatory drug (Acidic NSAID) typified by aspirin or indomethacin is also known, but it has less serious side effects than steroid while it is not appreciated to have sufficient effects on chronic inflammations such as rheumatism and deformation arthritis (or osteoarthritis). Further, whereas the acidic NSAID exerts slight side actions as compared with the steroid, it very often shows side effects such as intestinal canal trouble.

In view of such conventional technical problems as above, this invention has been made.

An object of this invention is to provide novel excellent phenylalkanoic acid derivatives which exhibit further remarkable antiphlogistic and analgesic actions as compared with said conventional phenylalkanoic acid-based non-steroid type antiphlogistic agents and have much less side effects such as gastro-intestinal tract trouble.

There are known methods for separating optical isomers which include a preferrential crystallization-out method, a diastereomer method and a chiral column operation method. These methods raise problems that they cannot provide enough optical purity to be used as a method for separating optical isomers from a phenylalkanoic acid derivative and they further need complicated treatments.

Further, as methods for separating optical isomers, there have recently be reported many methods utilizing asymmetry appreciating capability owned by organisms or enzymes. These methods are described in, for example, J. Chem. Soc., Commun., 148(1989) or J. Chem. Soc., Commun., 49(1990). At the present, however, since enzymes greatly vary in their selectivity or reactivity depending upon reaction conditions thereof or substrates therefor, general laws cannot be established. In other words, when an alkyl group, a halogen atom or the like which is apt to have solid (or three-dimensional) effects is present near the reaction site, an enzyme reaction may not satisfactorily proceed or may not proceed at all. Thus, at the present, the chemical structure of a substrate used, the kind, amount, reaction temperature and time of an enzyme used have great effects on the utilization of enzyme reaction. Accordingly, the above separating methods have been recognized as inappropriate to apply to such compounds having near the reaction site a substituent which is capable of exerting solid effects as the phenylalkanoic acid derivative of this invention. Thus, the separation of optical isomers of phenylalkanoic acid derivatives by using such separating methods as the above has been neither developed nor suggested.

Accordingly, another object of this invention is to provide a separating method for easily obtaining phenylalkanoic acid derivatives having high optical purity by conveniently separating the optical isomers of phenylalkanoic acid derivatives using high asymmetry appreciation capability owned by enzymes.

DISCLOSURE OF INVENTION

The present inventors first noted the chemical structure of phenylalkanoic acids and intensively investigated from the standpoint of relations between the structure and activity of said acid in attempts to find high-potency pharmacological activity of said acid. As a result of their investigation, they found that there had been neither synthesized nor pharmacologically investigated a compound prepared by introducing a cycloalkyl group including a keto group, hydroxy group or Ac-O-group (Ac: acyl group) onto the 4th position of a phenylalkanoic acid and further introducing a substituent onto the 3rd position thereof. At this point, they made intensive studies of a synthesizing method for introducing an alkoxyl group, nitro group or halogen atom as a substituent onto the 3rd position of the benzene ring which is the mother nucleus of the phenylalkanoic acid, and, as a result of their studies, they succeeded for the first time in synthesizing phenylalkanoic acid derivatives into which the above substituent(s) has(have) been introduced.

The phenylalkanoic acid derivatives so synthesized were then tested for their pharmacological activity with the result that phenylalkanoic acid derivatives having the above substituents, preferably a halogen atom, particularly preferably a chlorine or fluorine atom, introduced thereinto were unexpectedly found to be greatly improved in pharmacological activity and have specifically remarkable analgesic action and antiphlogistic action. In this manner, the present inventors found for the first time a phenylalkanoic acid derivative having such pharmacological activity as is not anticipated at all from heretofore known compounds similar to those of this invention, as well as a method for producing and separating said acid derivative, and further found that said acid derivative is useful as a non-steroid type antiphlogistic agent or analgesic agent. This invention is thus based on the above findings. Therefore, the substituents attached to the benzene ring of the phenylalkanoic acid derivative of this invention are very important component factors to complete this invention.

First, the phenylalkanoic acid derivatives of this invention will be explained hereunder in more detail.

The phenylalkanoic acid derivative of this invention is represented by the following formula (1)

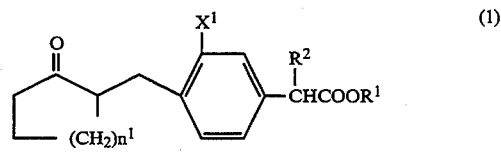

wherein $n^1$ is an integer of 1 to 2, $X^1$ is a halogen atom, alkoxyl group or nitro group, $R^1$ is a hydrogen atom or alkyl group and $R^2$ is a hydrogen or lower alkyl group. The acid derivative represented by the formula (1) is hereinafter referred to as "phenylalkanoic acid derivative I".

The phenylalkanoic acid derivative I will be further concretely explained below. In the formula (1), $X^1$ is a halogen atom selected from fluorine, chlorine, bromine and iodine atoms or an alkoxyl group selected from methoxyl, ethoxyl, propoxyl and other lower alkoxyl groups; $R^1$ may be an alkyl group selected from methyl, ethyl, n-propyl, iso-propyl, n-butyl, iso-butyl, tert-butyl, pentyl, hexyl, heptyl, octyl, nonyl, decyl, undecyl, dodecyl, tridecyl, tetradecyl, nonadecyl, eicocyl and other straight-chain or branched chain alkyl groups, as well as allcyclic alkyl groups represented by the following general formula (A)

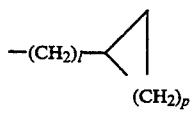

(A)

wherein 1 is an integer of 0–5 and p is an integer of 1–5; and $R^2$ is a lower alkyl group selected from methyl, ethyl, n-propyl, iso-propyl, n-butyl, iso-butyl, tert-butyl and other lower alkyl groups.

The phenylalkanoic acid derivative of this invention is also represented by the following formula (2)

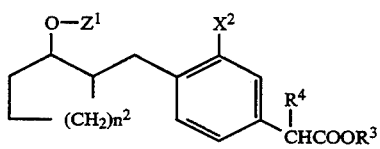

(2)

wherein $n^2$ is an integer of 1–2, $X^2$ is a halogen atom, alkoxyl group or nitro group, Z is a hydrogen atom or acyl group, and $R^3$ and $R^4$ may be identical with, or different from, each other and are each a hydrogen atom or alkyl group. Said acid derivative of the formula (2) is hereinafter referred to as "phenylalkanoic acid derivative II".

The phenylalkanoic acid derivative II will be further concretely be explained below.

Among various isomers covered by said acid derivatives II, those represented respectively by the following formulae (2a), (2b) and (2c) are preferred:

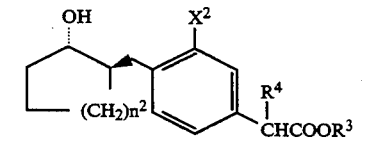

(2a)

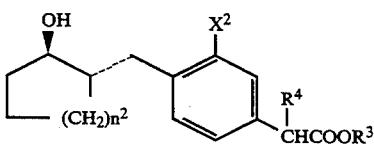

(2b)

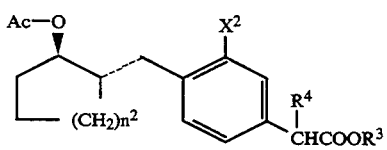

(2c)

In the above formulae (2a), (2b) and (2c), n is an integer of 1–2, $X^2$ is a halogen atom, alkoxyl group or nitro group, $R^3$ and $R^4$ may be identical with, or different from, each other and are a hydrogen atom or alkyl group, and Ac is an acyl group. These compounds respectively of the formulae (2a) to (2c) are a trans-coordinated phenylalkanoic acid derivative.

These phenylalkanoic acid derivatives II respectively of the above formula (2), (2a), (2b) and (2c) will further concretely be explained. In these formulae, $X^2$ is a halogen atom selected from fluorine, chlorine, bromine and iodine atoms, or an alkoxy group selected from methoxyl, ethoxyl, propoxyl, butoxyl and like groups, $R^3$ and $R^4$ are each an alkyl group selected-from methyl, ethyl, n-propyl, iso-propyl, n-butyl, iso-butyl, tert-butyl and like groups, and $Z^1$ (in case of an acyl group: Ac) is selected from acetyl, n-propionyl, iso-propionyl, n-butyroyl, iso-butyroyl, tert-butyroyl and other lower alkanoyl groups.

The phenylalkanoic acid derivatives of this invention represented by the formulae (1), (2), (2a), (2b) and (2c) include or cover their optical isomers and a mixture thereof due to the presence of asymmetric carbon atoms in said acid derivatives. In a case where the phenylalkanoic acid derivative is a racemic compound, it can be optically divided by use of a known method to obtain a d-body and l-body. It is preferred that the phenylalkanoic acid derivative II be treated by the later mentioned separating method according to this invention to separate optical isomers therefrom.

The phenylalkanoic acid derivatives of this invention can be converted into a physiocologically acceptable salt as required. Such salts include inorganic salts such as sodium, potassium, calcium, magnesium and aluminum salts; organic salts such as triethylamine, ethanolamine, dicyclohexylamine, piperidine and Tromethamine; and basic amino acid salts such as lysine and arginine, but physiocologically acceptable salts are not limited to the above-mentioned salts. In addition, the acid derivatives of this invention can also be converted to an inclusion compound by using cyclodextrine and the like to improve them in stability or solubility.

Next, the anti-inflammatory agents, analgesic agents and externally used preparations of this invention, each of which includes the phenylalkanoic acid derivative of this invention, will be explained hereunder.

It is possible that the phenylalkanoic acid derivatives of this invention are mixed with conventionally-used vehicle and take a form of various pharmatically acceptable medicines. When they are used as an antiphlogistic agent or analgesic agent, they may be administered either orally or non-orally. They may be orally administered in the form of a capsule, tablet, syrup, granule, grain, powder or the like and may be non-orally administered in the form of a cataplasm, ointment, gel, cream, gel-like cream, lotion, liniment, aerosol, plaster, suppository, eye drops, nasal drops, stomatic preparation, poultice and other externally-used preparations as well as in the form of injection.

The aforementioned preparations to be orally or non-orally administered can be made using a known base and based on a known formulation (Refer to, for example, (1) New Preparations Development System-Overall Techniques-Section of Bases and Additives, published on Jul. 12, 1985 by R & D Planning, (2) Recent Externally-Used Preparations for Skin, published on May 15, 1981 (First Edition) by Nanzando Bookstore, (3) The Eleventh Revised Japanese Pharmacopoeia Commentary published on Jul. 18, 1986 by Hirokawa Bookstore, (4) Pharmacology Pharmacy Pharmaceutics published in 1988 by Japan Industrial Technical Association and (5) Known Literature such as related literature, patent gazettes and magazines, which had been published before the present application was filed.

Compounds for the base for internally or externally used medicines exemplified by various preparations will be explained hereunder, but these compounds included in the base are no more than examples and are not particularly limited only if they may be pharmaceutically used.

First, the preparations for oral administration according to this invention will be explained hereunder.

For example, the phenylalkanoic acid derivatives of this invention are suitably mixed with an organic acid (such as citric acid, ascorbic acid, fumaric acid, tartaric acid, succinic acid, malic acid or adipic acid) or an antacid agent (such as sodium hydrogen carbonate, calcium hydrogen phosphate, magnesium metasilicate aluminate, magnesium hydroxide or synthetic hydrotalcite) to obtain medicinal compositions. These medicinal compositions or those incorporated with an optional additive can be formed into microcapsules by the use of a known method. Further, the above medicinal compositions are mixed, as required, with a suitable binder, lubricant, disintegrator, diluent or vehicle, dissolution rate-control agent, plasticizer, coloring agent, flavoring agent or the like and can then be made into preparations in the form of a tablet, granule or grain by the use of a known method. Furthermore, these preparations can be converted to those having prolonged action by being treated with a film forming agent to make the preparations be released gradually (the agent being such as a water-insoluble polymer including ethyl cellulose, an aminoalkylmethacrylate copolymer, polyvinyl acetate or polyethylene; an intra-intestinally soluble polymer including cellulose acetate phthalate, hydroxypropylmethyl cellulose phthalate, hydroxypropylmethyl cellulose acetate succinate, carboxymethylethyl cellulose, styrene-acryl copolymer, methacrylic acid copolymer, maleic anhydride copolymer or shellac; a paraffin wax including paraffin or microcrystalline wax; a higher alcohol including stearyl alcohol or cetanol; or an ester of a fatty acid including an ester of glycerin and a fatty acid, a hardened oil, carnauba wax or bees wax). The syrups according to this invention are formulated by mixing the above medicinal compositions with a glycide sweetening agent such as cane sugar or fruit sugar; a sugar alcohol-based sweetening agent such as sorbitol or maltitol; non-glycide natural sweetening agent such as a stevia extract or glycyrrhizin; or a synthetic or semi-synthetic sweetening agent such as saccharin or aspartame. Further, the preparations according to this invention may contain other vehicles or diluting agents such as cyclodextrin.

Thus, as the preparations for oral administration according to this invention, various preparations in the form of a capsule, tablet, granule, grain and syrup can be prepared by using a known base to be mixed and based on a known formulation for mixing.

Next, the eye drops according to this invention will be explained below. Aqueous bases for the eye drops are suitably incorporated with conventionally-used additives such as an isotonization agent, a buffer and a preservative. The isotonization agents are exemplified by sodium chloride, potassium chloride, polyhydric alcohols and saccharides. The buffers are exemplified by sodium borate, sodium citrate, sodium monohydrogen phosphate and sodium dihydrogen phosphate. The preservatives are exemplified by benzethonium chloride, benzalkonium chloride and chlorobutanol. Further, a stabilizer such as glycerin or polysorbate 80, a pH-control agent and the like may be added to the eye drops as required.

The components for the eye drops mentioned above may be suitably mixed with a conventionally-used base for an ointment, gel, suspension or the like to prepare an ointment, gel, suspension and other preparations.

The phenylalkanoic acid derivatives of this invention to be used for the aqueous eye drops are preferably in the form of an inorganic salt or an organic salt for the sake of easily formulating the eye drops, since these salts can be easily dissolved in water.

The injections according to this invention will be explained. The phenylalkanoic acid derivatives of this invention to be used for the injections are preferably in a water-soluble form, more preferably in the form of an inorganic salt or organic salt. The base for the injections may include a solvent and/or solubilizer, stabilizer, antiseptic and emulsifier and the like. The solvents and/or solubilizers are exemplified by glycols such as propylene glycol and glycerin; polyoxyalkylenes such as a poly (oxyethylene)-poly (oxypropylene) polymer, glycerin formal, benzyl alcohol and butanediol; vegetable oils such as soybean oil, cottonseed oil, rapeseed oil and safflower oil; triglycerides of middle-chain fatty acids having 8-12 carbon atoms (such as caprylic acid, capric acid and lauric acid), which are usually abbreviated as MCT; and mono- or diglycerides of fatty acids having 6-18 carbon atoms (such as caproic acid, capric acid, myristic acid, palmitic acid, linoleic acid and stearic acid). The stabilizers are exemplified by cholesterol, tocopherol, albumin, polysaccharides and sodium hydrogen sulfite. The antiseptics are exemplified by benzyl alcohol. The emulsifiers are exemplified by phospholipids such as yolk phospholipids, soybean phospholipids and phosphatidylcholine; and nonionic surfactants such as polyoxyalkylene copolymers (e.g.: polyoxyethylene-polyoxypropylene copolymer having an average molecular weight of 1,000-20,000), hardened castor oil polyoxyethylene-(40)-ether and hardened castor oil polyoxyethylene-(20)-ether. As required, said base may further include, as an isotonization agent, a polyhydric alcohol such as glycerin, sorbitol or xylitol; a monosaccharide such as grape sugar or fruit sugar; a sugar alcohol such as multose; and an amino acid such as L-alanine, L-valine or glycine; and it may also further include, as an adjuvant emulsifier, stearic acid, palmitic acid, linoleic acid, linolenic acid or salts thereof, phosphatidylethanol, phosphatidylserine or stearyl amine. The above-mentioned various compounds which may be included in the base are suitably selectively combined together thereby to prepare a base for aqueous or emulsified injections.

The plasters according to this invention will be explained. Compounds for the base for the plasters are suitably selected from known polymers (such as acrylic compositions which are copolymers with vinyl monomers such as methacrylic acid esters, acrylonitrile, vinyl acetate and vinyl propionate; silicone resin; polyisoprene rubber; polyisobutylene rubber; natural rubber; acrylic rubber; styrene-butadiene-styrene block copolymer; and styrene-isoprene-styrene block copolymer), fats and oils or higher fatty acids (such as almond oil, olive oil. tsubaki oil, persic oil, peanut oil, oleic acid, liquid paraffin and polybutene), tackifiers (such as rosin, rosin denatured maleic acid and hydrogenated rosin ester), and rash-preventing agents. The compounds selected for the base are incorporated with other additives (such as dl-camphor, l-menthol, thymol, nonylic acid vanlllylamldo, red pepper tincture, mentha oil and peppermint oil) as required, mixed with the phenylalkanoic acid derivative of this invention, and then suitably mixed with an ultraviolet light absorber or an antioxidant as required to obtain a mixture. The thus obtained mixture is applied on an expansible or non-expansible carrier (such as polypropylene, polyester, poly vinylidene chloride, polyacryl, polyurethane, rayon, cotton, ethylene-vinyl acetate copolymer, nonwoven fabric or nonwoven paper), after which a coating material which will be peeled off when used is stuck on the mixture applied to obtain a plaster.

The poultices according to this invention will be explained. Compounds for the base for the poultices are suitably selected from adhesive agents (such as synthetic water-soluble polymers including sodium polyacrylate, polyacrylic acid, poval, polyvinyl pyrrolidone, polyethylene oxide and polyvinyl methacrylate; natural products including arabic rubber, starch and gelatin; and others including methyl cellulose, hydroxypropyl cellulose, alginic acid, sodium alginate, ammonium alginate and sodium carboxymethyl cellulose), moistening agents (such as urea, glycerin, propylene glycol, butylene glycol and sorbitol), fillers (such as kaolin, zinc oxide, talc, titanium, bentonitc, epoxy resins, organic acids (citric acid, tartaric acid, maleic acid, succinic acid and the like), calcium, magnesium and aluminium), water, solubilizers (such as propylene carbonate, crotamiton and diisopropyl adipate), tackifiers (such as rosin, ester gum, polybutene and polyacrylic acid ester), rash-preventing agents (such as diphenhydramine hydrochloride, chlorpheniramine maleate, glycyrrhizic acid, dexamethasone, betamethasone and fluocinolone acetonide), and other additives (such as l-menthol, camphor, nonylic acid vanillylamido, thymol, red pepper extract and mentha oil). The compounds selected for the base are incorporated with the phenylalkanoic acid derivative of this invention and then suitably mixed with an ultraviolet light absorber or an antioxidant as required to obtain a poultice.

The ointments according to this invention will be explained. Compounds for the base for the ointments are selected from known or conventionally-used ones and preferably selected form the group of higher fatty acids and esters thereof (such as adipic acid, myristic acid, palmitic acid, stearic acid, oleic acid, adipic acid ester, myristic acid ester, palmitic acid ester, diethyl sebacate, hexyl laurate and cetyl isooctanate), waxes (such as spermaceti, beeswax and ceresine), surface active agents (such as polyoxyethylene alkyl ether phosphoric esters), higher alcohols (such as cetanol, stearyl alcohol and cetostearyl alcohol), silicone oils (such as dimethylpolysiloxane, methylphenylpolysiloxane, glycolmethylpolysiloxane and silicon glycol copolymer), hydrocarbons (such as hydrophilic vaseline, white vaseline, purified lanolin and liquid paraffin), water, humectants (such as glycerin, propylene glycol, butylene glycol and sorbitol), rash-preventing agents, and other additives (such as l-menthol, camphor and mentha oil). The compounds selected for the base are suitably mixed with the phenylalkanoic acid derivative of this invention to formulate preparations for percutaneous use, oral mucosa and rectum mucosa.

The gels according to this invention will be explained. Compounds for the base for the gels are selected from those included in known or conventionally-used various bases. Such a base may include lower alcohols (such as ethanol and isopropyl alcohol), water, gelatinizers (such as carboxyvinyl polymer, hydroxyethyl cellulose, ethyl cellulose, carboxymethyl cellulose and alginic acid propylene glycol ester), neutralizing agents (such as triethanolamine, diisopropanolamine and sodium hydroxide), surface active agents (such as sorbitan sesquioleate, sorbitan trioleate, sorbitan monooleate, sorbitan monostearate, sorbitan monolaurate, polyethylene glycol monostearate, polyoxyethylene nonylphenyl ether and polyoxyethylene lauryl ether), rash-preventing agents, and other additives (such as l-menthol, camphor and mentha oil). The compounds selected for the base are suitably mixed with the phenylalkanoic acid derivative of this invention to formulate preparations for percutaneous use, oral mucosa and rectum mucosa.

The creams according to this invention will be explained. Compounds for the base for the creams are selected from known or conventionally-used various bases. Such bases are exemplified by esters of higher fatty acids (such as myristic acid ester, palmitic acid ester, diethyl sebacate, hexyl laurate and cetyl isooctanate), lower alcohols (such as ethanol and isopropanol), hydrocarbons (such as liquid paraffin and squalane), polyhydric alcohols (such as propylene glycol and 1,3-butylene glycol), higher alcohols (such as 2-hexyl decanol, cetanol and 2-octyl dodecanol), emulsifiers (such as polyoxyethylene alkyl ethers, fatty acid esters and polyethylene glycol fatty acid esters), antiseptics (such as para-hydroxybenzoic acid ester), rash-preventing agents, and other additives (such as l-menthol, camphor and mentha oil). The compounds selected for the base are incorporated with the phenylalkanoic acid derivative of this invention and then suitably mixed with an ultraviolet light absorber or an antioxidant as required to obtain a cream.

Further, the gel-like creams according to this invention having properties which are intermediate between those of cream and gel, can be obtained by mixing the cream mentioned above with a gelatinizer (such as carboxyvinyl polymer, hydroxyethyl cellulose, hydroxypropyl cellulose, ethyl cellulose or carboxymethyl cellulose) and a neutralizing agent (such as diisopropanolamine, triethanolamine or sodium hydroxide) and then adjusting the whole to a pH value of 4–8, preferably 5–6.5.

The above base for the creams or gel-like creams is suitably mixed with the phenylalkanoic acid derivative of this invention to formulate preparations for percutaneous use, oral mucosa and rectum mucosa.

The liniments according to this invention will be explained. The phenylalkanoic acid derivative of this invention is incorporated with an alcohol (such as a monohydric alcohol including ethanol, propanol or isopropanol or a polyhydric alcohol including polyethylene glycol, propylene glycol or butylene glycol), water, a fatty acid ester (such as an ester of adipic acid, sebacic acid or myristic acid) and a surface active agent (such as polyoxyethylene alkyl ether), and further mixed with an ultraviolet light absorber and an antioxidant as required thereby to obtain a liniment of this invention.

The liniments of this invention may contain, as required, a neutralizing agent to be used for adjustment of pH, a viscosity-increasing agent (such as methyl cellulose, carboxyvinyl polymer or hydroxypropyl cellulose), a rash-preventing agent and other additives (such as l-menthol, camphor, mentha oil, red pepper extract, nonylic acid vanillylamido, thymol, crotamiton, propylene carbonate or diisopropyl adipate.

The suppositories according to this invention will be explained. Compounds for the base for the suppositories are suitably selected from synthetic fat and oil-based compounds such as cacao butter, hydrogenated peanut oil and hydrogenated coconut oil; and water-soluble compounds such as polyethylene glycols, Monolen, Tween and Pluronic.

The nasal drops according to this invention will be explained. The phenylalkanoic acid derivative of this invention is dissolved, suspended or emulsified in water, a buffer solution {such as Sorensen buffer solution [Ergeb. physiol. 12, 393 (1912)], Clark-Lubs buffer solution [J. Bact. 2, (1), 109,191 (1917)], Macll-vaine buffer solution [J. Biol, Chem. 49, 183 (1921)], Michaelis buffer solution [Die Wasserstoffionen Komzentration, p. 186 (1914)] or Kolthoff buffer solution [Bio-Chem. Z. 179, 410 (1926)]}, or a water-containing solution thereby to formulate an aqueous liquid preparation for use as nasal drops. Further, the phenylalkanoic acid derivative of this invention is suspended or emulsified in an oily base (such as sesame oil, olive oil, corn oil, soybean oil, cottonseed oil, peanut oil, lanolin, vaseline, paraffin, Isopar, silicone oil, a middle-chain fatty acid, or a glycerin ester or an alcohol ester of the fatty acid) thereby to formulate an oily suspension preparation.

The semisolid preparations (ointments, gels or creams) can be formulated by the use of the above-mentioned compounds for the base for ointments, gels or creams, respectively. Further, in case of the liquid-like preparations, they are preferably filled into a vessel for nasal drops, a spray vessel or other similar vessels which is suitable for applying such preparation into a nasal cavity, in order to facilitate the preparations to be dropped or sprayed into a nasal cavity when administered.

The aerosols according to this invention are formulated by the use of a base including a spraying agent such as liquefied natural gas, dimethyl ether, carbonic acid gas or flon gas, as well as a diluent.

The stomatic adhesive preparation according to this invention will be explained. The phenylalkanoic acid derivative of this invention is incorporated in a base suitably including a hydrophilic polymer (such as hydroxypropyl cellulose, an acrylic acid copolymer, a carboxyvinyl polymer, polyvinyl pyrrolidone, polyvinyl alcohol, polyethylene glycol, alginic acid or a salt thereof, a maleic anhydride-methylvinyl ether copolymer, chitosan, a derivative of chitosan, a vinyl acetate copolymer, agar, gluten or gelatin), an antibacterial agent, a softening agent, a surface active agent, a cross-linking agent, a neutralizing buffering agent, a filler, a perfume, a coloring agent, a tasting agent and other compounds such as a diluent, thereby to obtain an adhesive tablet or a film-like adhesive plaster.

When the phenylalkanoic acid derivatives of this invention are administered as an oral preparation, an injection or a preparation for external use, they will effectively act on chronic rheumatism, osteoarthritis, lumbago, scapula periarthritis, sore throat, acute otitis media, toothache, gout, shoulder periarthritis, peritendinitis, muscleache, traumatic swelling, dolor, distortion, bruise, torn-muscle, sprained-finger, condylus humeri inflammation and the like.

The dose of each preparation of this invention is suitably decided in view of the condition, age, sex and the like of an object or patient to which the preparation will be administered. The preparation of this invention is preferably administered in a dose of about 1–100 mg (the amount of phenylalkanoic acid derivative) per one time and about one to three times per day thereby to achieve good effects.

Next, methods for the production of the phenylalkanoic acid derivatives of this invention will be explained hereunder. The phenylalkanoic acid derivatives of this invention can be obtained in a very good yield in accordance with the following production methods and, however, they can also be produced by other methods chemically similar to the following ones or other methods quite different from the following ones.

First, methods for producing a phenylalkanoic acid derivative I of this invention (Production Methods 1–3) will be explained hereunder.

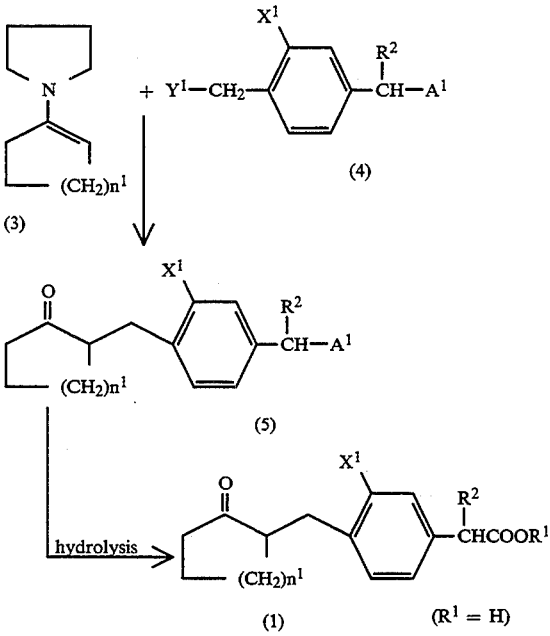

In the reaction sequence of Preparation Method 1, $Y^1$ is a halogen atom, $A^1$ is CN, $CONH_2$ or $COOR^1$, and $n^1$, $X^1$, $R^1$ and $R^2$ are as defined before.

An enamine (3) prepared from a cycloalkanone (cyclopentanone or cyclohexanone) and pyrrolidine, and a compound (4) are reacted with each other in an inert solvent (such as benzene, toluene, dioxane or dichloromethane) at a reaction temperature of 20°–130° C. for 0.5–10 hours and then treated with diluted hydrochloric acid to obtain a compound (5). In a case where the $A^1$ portion of the compound (5) is CN, $CONH_2$ or $COOR^1$ ($Ri^1 \neq H$), the compound (5) is hydrolyzed in the presence of an inorganic base (such as sodium hydroxide, potassium hydroxide or potassium carbonate) or an inorganic acid (such as hydrochloric acid or sulfuric acid) in water or a water-containing alcohol at a reaction temperature of 20°–120° C. for 0.5–10 hours thereby to obtain a compound (1) ($R^1=H$).

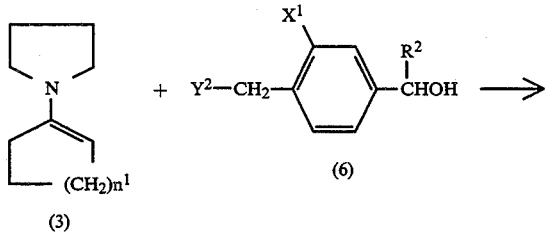

-continued
Preparation Method 2

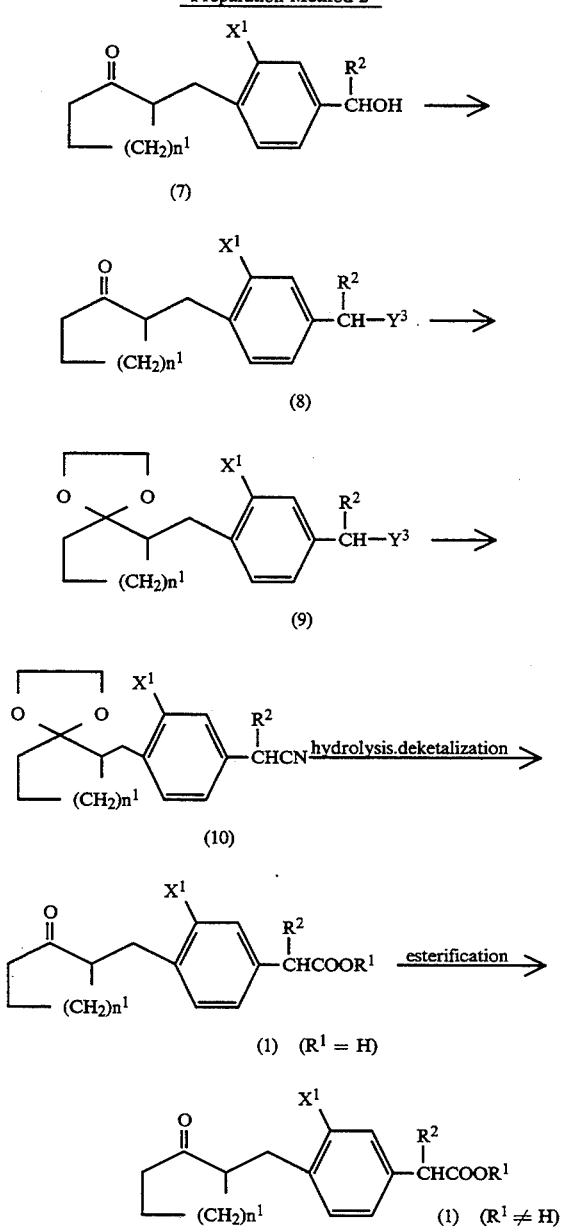

Preparation Method 3

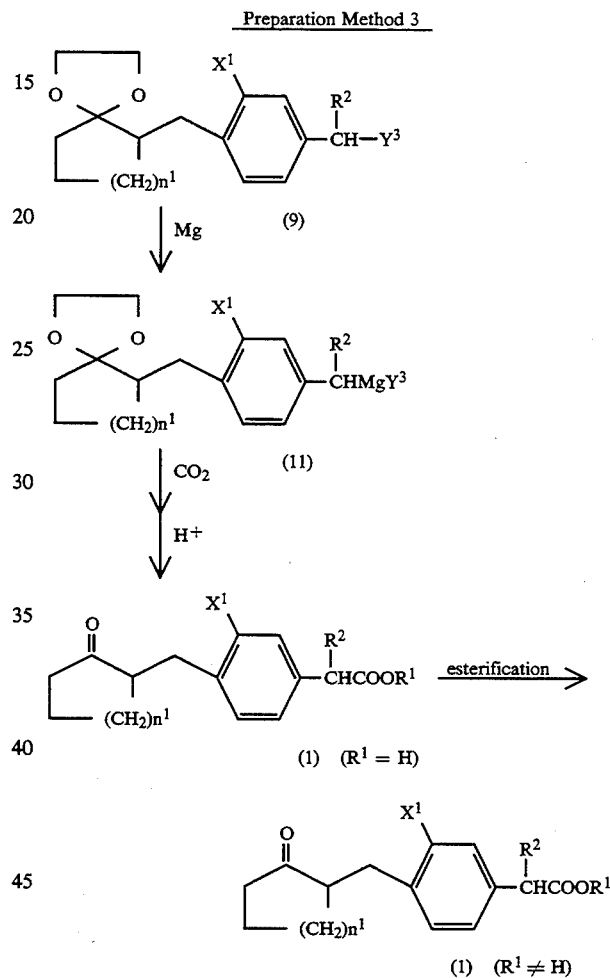

dimethyl sulfoxide, dimethylformamide, acetonitrile, ethanol or water) to obtain a compound (10). The compound (10) is then hydrolyzed and deketalized in an inorganic acid (such as sulfonic acid, acetic acid or hydrochloric acid) thereby to obtain a compound (1) ($R^1$=H). Further, it is also possible to convert the compound (1) ($R^1$=H) to an ester body by a known esterification method thereby to obtain a compound (1) ($R^1 \neq H$).

In the reaction sequence of Preparation Method 2, $Y^2$ and $Y^3$ are each a halogen atom, and $n^1$, $X^1$, $R^1$ and $R^2$ are as defined before An enamine (3) prepared from a cycloalkanone and pyrolidine, and a compound of the formula (6) are reacted together in an inert solvent (such as benzene, toluene, dioxane or dichloromethane) and then treated with diluted hydrochloric acid to obtain a compound (7). The thus obtained compound (7) is treated with a halogenating agent (such as phosphorus tribromide, phosphorus oxychloride, thionyl chloride, hydrochloric acid or hydrobromic acid) in the presence or absence of an inert solvent (such as chloroform, carbon tetrachloride, benzene, toluene or sulfuric acid) to obtain a compound (8). The compound (8) is reacted with ethylene glycol to obtain a ketal body (9) which is then reacted with sodium cyanide in an inert solvent (such as In the reaction sequence of Preparation Method 3, $n^1$, $X^1$, $Y^3$, $R^1$ and $R^2$ are as defined before The compound (9) is reacted with magnesium in an inert solvent (such as diethyl ether or tetrahydrofuran) to obtain Grignard's reagent (11) which is then reacted with carbonic acid gas or solid carbon dioxide in the absence of a solvent or in the presence of an inert solvent and then decomposed and deketalized by the use of an inorganic acid (such as hydrochloric acid or sulfuric acid) thereby to obtain a compound (1) ($R^1$=H). Further, it is also possible to convert the compound (1) ($R^1$=H) to an ester body in accordance with a known esterification thereby to obtain a compound (1) ($R^1 \neq H$).

Next, a method for producing a phenylalkanoic acid derivative II of this invention (Preparation Method 4) will be explained hereunder.

Preparation Method 4

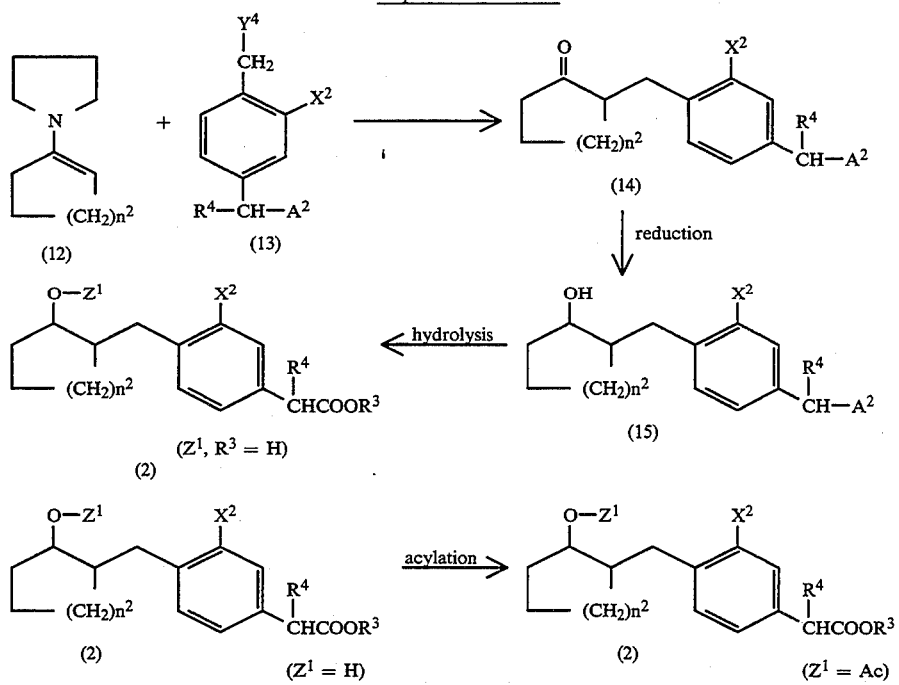

In the reaction sequence of Preparation Method 4, $Y^4$ is a halogen atom, $A^2$ is CN, $CONH_2$ or $COOR^3$, and $n^2$, $X^2$, $Z^1$, $R^3$, $R^4$ and Ac are as defined before.

An enamine (12) prepared from a cycloalkanone and pyrrolidine, and a compound (13) are reacted with each other in an inert solvent (such as benzene, toluene, dioxane or dichloromethane) at a reaction temperature of 20°–130° C. for 0.5–10 hours and then treated with diluted hydrochloric acid to obtain a compound (14). The thus obtained compound (14) is reduced with a reducing agent (such as a boron hydride compound including sodium boron hydride or sodium cyanoboron hydride) in an inert solvent (such as methanol, ethanol, DMF or DMSO) at a reaction temperature of 20°–100° C. for 0.5–3 hours to obtain a compound (15). In a case where the $A^2$ portion of the compound (15) is CN, $CONH_2$ or $COOR^3$ ($R^3 \neq H$), the compound (15) is hydrolyzed in the presence of an inorganic base (such as sodium hydroxide, potassium hydroxide or potassium carbonate) or an inorganic acid (such as hydrochloric acid or sulfuric acid) in water or a water-containing alcohol at a reaction temperature of 20°–120° C. for 0.5–10 hours thereby to obtain a compound (2) ($Z^1$, $R^3$=H) Further it is also possible to acylate the compound (2) ($Z^1$=H) with an acyl chloride (such as acetyl chloride, propionyl chloride or butyroyl chloride) in the presence of a tertiary amine (such as triethylamine or pyridine) in an inert solvent (such as ether, chloroform or benzene) thereby to obtain a compound (2) ($Z^1$=Ac).

Next, a method for the separation of optical isomers of a phenylalkanoic acid derivative of this invention will be explained hereunder. Such method of this invention is particularly useful for the separation of optical isomers of a phenylalkanoic acid derivative II.

In conventional methods for the separation of optical isomers utilizing enzymes, in view of the deactivation and the like of the enzymes, the optical isomers have generally been separated by the use of the selective hydrolysis of an ester (an acyl group) in the isomers in an aqueous solution. However, in the method for the separation of this invention, the optical isomers are separated by the use of a reaction opposite to the above hydrolysis, that is the selective acylation (asymmetric esterification) of the isomers in an organic solvent. Further, in spite of the conventional recognition that enzymes generally deteriorate in their reactivity or selectivity when a substituent, such as halogen, being apt to have steric or solid effects is present near the reaction site of the substrate, an asymmetric esterification proceeds at a surprisingly high selectivity in the method for the separation of this invention mentioned hereunder. This fact is a very important component factor to complete this invention.

The method for the separation of optical isomers of this invention will be explained hereunder in more detail.

Separation Method

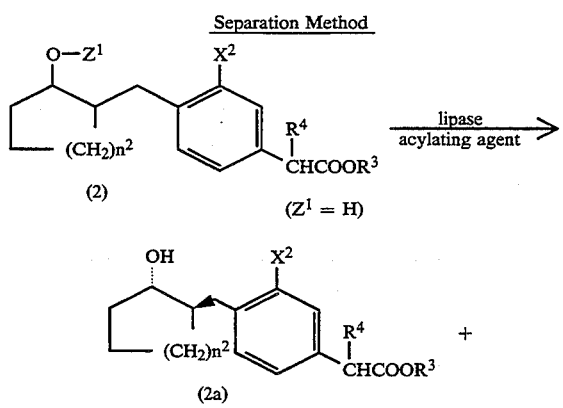

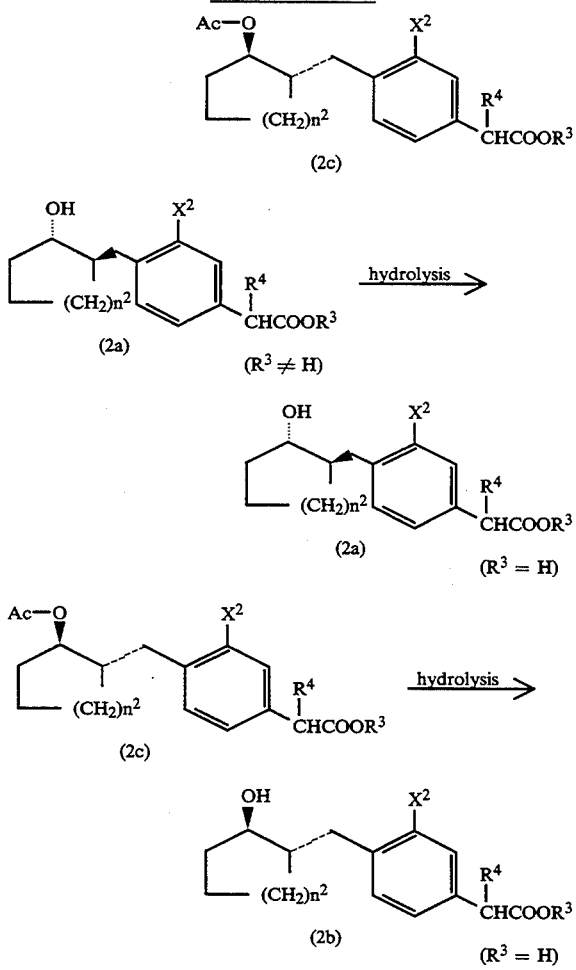

In the reaction sequence of the above Separation Method, $n^2$, $X^2$, $Z^1$, $R^3$, $R^4$ and Ac are as defined before.

The trans-form phenylalkanoic acid derivative represented by the formula (2) ($Z^1$=H) is reacted with an acylating agent (such as vinyl acetate, isopropenyl acetate or vinylpropionate) in the presence of lipase which is an enzyme in an organic solvent (such as diethyl ether, tert-butylmethyl ether, dichloromethane or acetone) at a temperature of 20°-60° C. for 1–10 days thereby to acylate only the hydroxyl group of R-conformation. Subsequently, the optical isomers (2a) and (2c) are easily separated from each other by column chromatography or fractional distillation. Further, in a case where the isomers (2a) and (2c) are ester bodies ($R^3 \neq H$), these isomers (2a) and (2c) are hydrolyzed by a known hydrolysis method thereby to obtain a compound of the formula (2a) ($R^3$=H) and a compound of the formula (2b) ($R^3$=H), respectively.

BEST MODE FOR CARRYING OUT THE INVENTION

This invention will be explained in more detail by reference to the following Reference Examples and Examples, but this invention is not limited to the embodiments described in the Examples.

In the following Reference Examples and Examples, the distillation under a reduced pressure is effected using a glass tube oven (Tradename of GTO-250R rotation type) produced by Shibata Kagaku Kikai Kogyo Co., Ltd., Japan, and the distillation temperature (the boiling point of the resulting compound) is shown by the temperature of the column.

REFERENCE EXAMPLE 1

Fifty (50) g of 3-chloro-4-methylpropiophenone, 134 g of lead tetraacetate and 500 ml of methyl orthoformate were mixed together to obtain a mixed liquid which was then incorporated dropwise with 46 ml of perchloric acid at a temperature of −5° to 0° C. while agitating, after which the whole was agitated at 50° C. for two hours, freed of the solvent at a reduced pressure and then extracted with 500 ml of ethyl acetate. The extract obtained was washed with water, dried, freed of the solvent and thereafter distilled at a reduced pressure thereby to obtain 48 g of methyl-2-(3-chloro-4-methylphenyl) propionate having a boiling point of 103°°–108° C./2–3 mmHg.

REFERENCE EXAMPLE 2

Fifty (50) g of methyl-2-(3-chloro-4-methylphenyl)-propionate, 42 g of N-bromosuccinimide and 600 ml of carbon tetrachloride were mixed together to form a mixed liquid which was then incorporated with a catalytic amount of benzoyl peroxide and refluxed under agitation for one hour. After the end of the reaction, the reaction mixture was filtered to remove insolubles and obtain a filtrate which was then freed of the solvent at a reduced pressure. The residue obtained was introduced into a silica gel-packed column to be adsorbed thereon and then eluted with isopropyl ether-hexane (1:10) to obtain an eluate. The thus obtained eluate was freed of the solvent thereby to obtain 31 g of methyl-2-(4-bromomethyl-3-chlorophenyl)propionate.

REFERENCE EXAMPLE 3

Forty-five (45) grams of 1-pyrrolidino-1-cyclohexene, 50 g of 1-(4-bromomethyl-3-chlorophenyl) ethanol and 300 ml of dichloromethane were mixed together to obtain a mixed liquid which was refluxed under agitation for two hours. After the end of the reaction, the reaction mixture was incorporated with diluted hydrochloric acid, agitated at room temperature for 30 minutes, treated to separate the organic layer therefrom, washed with water, dried and then freed of the solvent to obtain a residue. The thus obtained residue was adhered to a column packed with silica gel and then eluted with ethyl acetate.hexane (⅓) to obtain an eluate which was freed of the solvent to obtain 38.5 g of 1-[3-chloro-4-(2-oxocyclohexane-1-yl methyl) phenyl]ethanol.

REFERENCE EXAMPLE 4

Forty (40) grams of 1-[3-chloro-4-(2-oxocyclohexane-1-yl methyl)phenyl]ethanol were dissolved in 300 ml of carbon tetrachloride and then incorporated dropwise with 44.7 g of phosphorus tribromide at a temperature of −15° to −10° C., after which the whole was stirred at said temperature for 30 minutes, withdrawn from the ice bath and then further stirred for one hour. After the completion of the reaction, the reaction mixture was water washed, dried and then freed of the solvent at a reduced pressure to obtain a residue. The residue was adhered to a silica gel-packed column and then eluted with isopropyl ether-hexane (⅓), after which the eluate was freed of the solvent thereby to obtain 46.5 g of 1-[3-chloro-4-(2-oxocyclohexane-1-yl methyl)-phenyl]ethylbromide.

REFERENCE EXAMPLE 5

Forty-five (45) grams of 1-[3-chloro-4-(2-oxocyclohexane-1-yl methyl)phenyl]ethylbromide were dissolved in 200 ml of benzene and then incorporated with 12.7 g of ethylene glycol and 0.12 g of p-toluenesulfonic acid, after which the whole was refluxed under agitation for 4 hours. After the end of the reaction, the reaction mixture was washed with water, an aqueous solution of sodium hydrogen carbonate and water in this order. Then, the organic layer obtained was dried and thereafter freed of the solvent at a reduced pressure thereby to obtain 51 g of 1-[3-chloro-4-(2,2-ethylenedioxycyclohexane-1-yl methyl)phenyl]ethylbromide.

REFERENCE EXAMPLE 6

7.35 g of sodium cyanide were dissolved in 10 ml of water under heat, incorporated with 60 ml of dimethylsulfoxide, cooled to room temperature and then incorporated with a solution of 51 g of 1-[3-chloro-4-(2,2-ethylenedioxycyclohexane-1-yl methyl)phenyl]ethyl bromide in 90 ml of dimethylsulfoxide. The reaction mixture obtained was agitated at 70° C. for one hour, thereafter incorporated with water and extracted with ethyl acetate. The extract was washed with water, dried and then freed of the solvent at a reduced pressure to obtain a residue. The thus obtained residue was adhered to a silica gel-packed column and then eluted with isopropyl ether hexane (2/1). The eluate obtained was freed of the solvent thereby to obtain 32.7 g of 2-[3-chloro-4-(2,2-ethylenedioxycyclohexane-1-yl methyl)phenyl]propionitrile.

Example 1

4.4 g of 1-pyrrolidino-1-cyclohexene, 6 g of methyl-2-(4-bromomethyl-3-chlorophenyl)propionate and 20 ml of dioxane were mixed together to obtain a mixed liquid which was refluxed under agitation for 4 hours. After the end of the reaction, the reaction mixture obtained was incorporated with diluted hydrochloric acid and then extracted with 100 ml of ethyl acetate. The extract obtained was washed with water, dried, freed of the solvent and then distilled at a reduced pressure thereby to obtain 4.6 g (in a yield of 73%) of oily methyl-2-[3-chloro-4-(2-oxocyclohexane-1-yl methyl)phenyl]propionate.

The boiling point and instrumental analyses of the thus obtained final compound are indicated hereunder.

Boiling point 156°–161° C./3 mmHg
IR spectra 1740 cm$^{-1}$ (—COO—) 1713 cm$^{-1}$ (C=O)
Mass spectrum (m/e) 308(M+)
Elemental analysis $C_{17}H_{21}ClO_3$ Found C: 66.25 H: 6.82 Theoretical C: 66.12 H: 6.85
$^1$H NMR spectra(CDCl$_3$, δ) 1.47(3H,d,J=7.33 Hz), 1.35–2.45(8H,m), 2.53(1H,dd,J=8.06,13.74 Hz), 2.60–2.75(1H,m), 3.29(1H,dd,J=5.13,13.56 Hz), 3.66(3H,s), 3.67(1H,g,J=7.14 Hz), 7.10(1H,dd,J=1.83,7.87 Hz), 7.20(1H,d,J=7.88 Hz), 7.28(1H,d,J=1.83 Hz)

Example 2

4.5 g of methyl-2-[3-chloro-4-(2-oxocyclohexane-1-yl methyl)phenyl]propionate were incorporated with 80 ml of an aqueous methanol containing 1.8 g of sodium hydroxide and then refluxed under heat for two hours. After the end of the reaction, the reaction mixture was treated to concentrate the solvent at a reduced pressure, incorporated with 50 ml of water, washed with 50 ml of ethyl acetate, treated to adjust the aqueous layer thereof to a pH of 2 with concentrated hydrochloric acid, extracted with 50 ml of ethyl acetate, washed with water, dried and then freed of the solvent to obtain a residue. The thus obtained residue was recrystallized from isopropyl ether to obtain 3.9 g (in a yield of;91%) of 2-[3-chloro-4-(2-oxocyclohexane-1-yl methyl)phenyl]propionic acid.

The melting point and instrumental analyses of the thus obtained final compound are indicated below.

Melting point 104°–107 ° C.
IR spectrum 1702 cm$^{-1}$ (—COOH, >C=O)
Mass spectrum (m/e) 294(M+)
Elemental analysis $C_{16}H_{19}ClO_3$ Found C: 65.22 H: 6.48 Theoretical C: 65.19 H: 6.50
$^1$H NMR spectra (CDCl$_3$, δ) 1.48(3H,d,J=7.3 Hz), 1.38–2.45(8H,m), 2.53(1H,dd,J=8.1,13.6 Hz), 2.65(1H,m), 3.29(1H,dd,J=4.8,13.6 Hz), 3.68(1H,q,J=7–3HZ), 7.11(1H,dd,J=1.8,8.1 Hz), 7.20(1H,d,J=8.1 Hz), 7.30(1H,d,J=1.8HZ)

Example 3

5 g of methyl-2-[3-chloro-4-(2-oxocyclopentane-1-yl methyl)phenyl]propionate were incorporated with 80 ml of an aqueous methanol containing 2.9 g of potassium hydroxide and then refluxed under heat for two hours. After the completion of the reaction, the reaction mixture obtained was treated to concentrate the solvent at a reduced pressure, incorporated with 50 ml of water, washed with 50 ml of ethyl acetate, after which the aqueous layer obtained was adjusted to a pH of 2 with conc. hydrochloric acid, thereafter extracted with 60 ml of ether, washed with water, dried and then freed of the solvent to obtain a residue. The thus obtained residue was distilled at a reduced pressure thereby to obtain 4.2 g (yield 88%) of oily 2-[3-chloro-4-(2-oxocyclopentane-1-yl methyl)phenyl]propionic acid.

The final compound so obtained had the following boiling point and instrumental analyses.

Boiling point 150°–153° C./0.2 mmHg
IR spectrum 1740, 1711 cm$^{-1}$ (—COOH, >C=O)
Mass spectrum (m/e) 280(M+)
Elemental analysis $C_{15}H_{17}ClO_3$ Found C: 64.21 H: 6.11 Theoretical C: 64.17 H: 6.10
$^1$H NMR spectra (CDCl$_3$, δ) 1.50(3H,d,J=7.3 Hz), 1.5–2.2(7H,m), 2.5–3.3 (2H,m), 3.69(1H,q,J=7.3 Hz), 7.13(1H,dd,J=1.7 Hz,7.9 Hz), 7.18(1H,d,J=7.9 Hz), 7.29(1H,d,J=1.5 Hz)

Example 4

5 g of 2-[3-chloro-4-(2,2-ethylenedioxycyclohexane-1-yl methyl)phenyl]propionitrile were incorporated with 30 ml of acetic acid and 25 ml of 50% sulfuric acid and then refluxed under agitation for 4 hours. After the end of the reaction, the reaction, mixture was concentrated at a reduced pressure, incorporated with 50 ml of dichloromethane and washed with water, after which the organic layer obtained was extracted with a 6N-sodium hydroxide aqueous solution. The aqueous layer obtained was washed with dichloromethane, acidified with a 6N-hydrochloric acid and then extracted with 50 ml of dichloromethane. Then, the extract was washed with water, dried and freed of the solvent to obtain a residue which was then recrystallized from isopropyl ether thereby to obtain 3.8 g (yield 83%) of 2-[3-chloro-4-(2-oxocyclohexane-1-yl methyl)phenyl] propionic acid.

The melting point and instrumental analyses of the thus obtained final compound are as follows.

Melting point 104°–107° C.

Elemental analysis $C_{16}H_{19}ClO_3$ Found C: 65.17 H: 6.51 Theoretical C: 65.19 H: 6.50

The IR, Mass and $^1H$ NMR data for the above final compound agreed with those for the final compound obtained in Example 2.

Example 5

5.6 g of 1-[3-chloro-4-(2,2-ethylenedioxycyclohexane-1-yl methyl)phenyl]ethyl bromide were dissolved in 50 ml of tetrahydrofuran and added dropwise over one hour to 0.55 g of magnesium suspended in 10 ml of tetrahydrofuran, after which the whole was refluxed under agitation for three hours and cooled to produce a Grignard's reagent. The Grignard's reagent so produced was poured onto an excessive amount of solid carbon dioxide and allowed to stand still for 4 hours, after which the whole was acidified with diluted hydrochloric acid and extracted with 100 ml of ether. The extract obtained was concentrated to obtain a residue which was then incorporated with 25 ml of acetic acid and 10 ml of water and refluxed under agitation for two hours. After the end of the reaction, the reaction mixture was incorporated with 100 ml of water and extracted with 50 ml of ether. The extract obtained was washed with water, dried and freed of the solvent to obtain a residue which was then recrystallized from isopropyl ether thereby to obtain 2.7 g (yield 61%) of 2-[3-chloro-4-(2-oxocyclohexane-1-yl methyl)phenyl] propionic acid.

The thus obtained final compound had the following melting point and instrumental analyses.

Melting point 104°–107° C.

Elemental analysis $C_{16}H_{19}ClO_3$ Found C: 65.08 H: 6.48 Theoretical C: 65.19 H: 6.50

The IR, MASS and $^1H$ NMR data for the above final compound agreed with those for the final compound obtained in Example 2.

Examples 6–22

The compounds indicated in the following Table 1 were synthesized in accordance with the methods of Examples 1–5. Table 1 further indicates the $n^1$, $X^1$, $R^1$ and $R^2$ in the general formula of these compounds as well as the melting point or boiling point and elemental analysis thereof.

TABLE 1

| Example | $n^1$ | $X^1$ | $R^1$ | $R^2$ | M.P. or B.P.[a](°C.) | Theoretical (%) C | H | N | Found (%) C | H | N |
| --- | --- | --- | --- | --- | --- | --- | --- | --- | --- | --- | --- |
| Ex. 6 | 1 | F | H | $CH_3$ | 138~140/0.2 mmHg | 68.17 | 6.48 | 0 | 68.26 | 6.49 | 0 |
| Ex. 7 | 1 | $OCH_3$ | H | $CH_3$ | 150~155/0.2~0.3 mmHg | 69.55 | 7.30 | 0 | 69.67 | 7.28 | 0 |
| Ex. 8 | 1 | $NO_2$ | H | $CH_3$ | Oily | 61.85 | 5.88 | 4.81 | 61.99 | 5.84 | 4.93 |
| Ex. 9 | 1 | Cl | H | H | 128~131 | 63.04 | 5.67 | 0 | 63.00 | 5.67 | 0 |
| Ex. 10 | 2 | F | H | $CH_3$ | 147~150/0.2 mmHg | 69.05 | 6.88 | 0 | 68.98 | 6.90 | 0 |
| Ex. 11 | 2 | $OCH_3$ | H | $CH_3$ | 98~101 | 70.32 | 7.64 | 0 | 70.19 | 7.65 | 0 |
| Ex. 12 | 2 | $NO_2$ | H | $CH_3$ | Oily | 62.94 | 6.27 | 4.59 | 63.08 | 6.30 | 4.50 |
| Ex. 13 | 2 | Br | H | $CH_3$ | 90~92 | 56.65 | 5.65 | 0 | 56.76 | 5.67 | 0 |
| Ex. 14 | 2 | Cl | H | H | 148~150 | 64.17 | 6.10 | 0 | 64.16 | 6.11 | 0 |
| Ex. 15 | 2 | Cl | $C_2H_5$ | $CH_3$ | 167~170/2 mmHg | 66.97 | 7.18 | 0 | 67.16 | 7.21 | 0 |
| Ex. 16 | 2 | Cl | n-$C_3H_7$ | $CH_3$ | 172~173/1.5 mmHg | 67.75 | 7.48 | 0 | 67.60 | 7.53 | 0 |
| Ex. 17 | 2 | Cl | i-$C_3H_7$ | $CH_3$ | 180~190/2 mmHg | 67.75 | 7.48 | 0 | 67.89 | 7.47 | 0 |
| Ex. 18 | 2 | Cl | i-$C_5H_{11}$ | $CH_3$ | 185~189/3 mmHg | 69.12 | 8.01 | 0 | 69.07 | 8.06 | 0 |
| Ex. 19 | 2 | Cl | cyclohexyl | $CH_3$ | 153~156/0.2 mmHg | 70.10 | 7.75 | 0 | 70.23 | 7.81 | 0 |
| Ex. 20 | 2 | Cl | n-$C_8H_{19}$ | $CH_3$ | 175~182/0.3~0.6 mmHg | 70.83 | 8.67 | 0 | 70.96 | 8.71 | 0 |
| Ex. 21 | 2 | Cl | n-$C_{12}H_{25}$ | $CH_3$ | 218~220/1.5 mmHg | 72.62 | 9.36 | 0 | 72.79 | 9.40 | 0 |
| Ex. 22 | 2 | Cl | n-$C_{17}H_{35}$ | $CH_3$ | 34~36 | 74.33 | 10.02 | 0 | 74.39 | 10.00 | 0 |

[a] B.P. indicates the column temperature of glass tube oven.

Example 23

6 g of methyl-2-[3-chloro-4-(2-oxocyclohexane-1-yl methyl)phenyl]propionate were dissolved in 30 ml of methanol and then incorporated with 0.75 g of sodium boron hydride under agitation at room temperature, agitated at room temperature for 30 minutes, incorporated with 100 ml of water and then extracted with 100 ml of ethyl acetate. The extract obtained was washed with water, dried and then freed of the solvent at a reduced pressure to obtain a mixture of trans-form and cis-form bodies. The thus obtained mixture was absorbed onto a silica gel-packed column and then separated with ethyl acetate-hexane (1:3) to obtain 1.8 g (yield 30%) of methyl-2-[3-chloro-4-(cis-2-hydroxycyclohexane-1-yl methyl)phenyl]propionate and 3.0 g (yield 50%) of methyl-2-[3-chloro-4-(trans-2-hydroxycyclohexane-1-yl methyl) phenyl]propionate.

The cis-form compound so obtained was oily and the instrumental analyses thereof are as follows.

IR spectra 1740 cm$^{-1}$ (COO) 3420 cm$^{-1}$ (OH)
Mass spectrum (m/e) 310 (M+)
Elemental analysis $C_{17}H_{23}ClO_3$ Found C: 65.48 H: 7.51 Theoretical C: 65.69 H: 7.46
$^1$H NMR spectra (CDCl$_3$, δ) 1.51(3H,d,J=7.3HZ), 1.25–1.79(9H,m), 2.60–2.86(2H,m), 3.66(3H,s), 3.67($^1$H,q,J=7.3 Hz), 3.72–3.82($^1$H,m), 7.10–7.29(3H,m,Ar—H)

The trans-form compound so obtained was also oily and the instrumental analyses thereof are as follows.

IR spectra 1740 cm$^{-1}$ (COO) 3420 cm$^{-1}$ (OH)
Mass spectrum (m/e) 310 (M+)
Elemental analysis $C_{17}H_{23}ClO_3$ Found C: 65.88 H: 7.40 Theoretical C: 65.69 H: 7.46
$^1$H NMR spectra (CDCl$_3$, δ) 1.48(3H,d,J=7.0 Hz), 0.93–2.04(9H,m), 2.40($^1$H,dd,J=9.7,13.37 Hz), 3.35($^1$H,dd,J=3.85,13.38 Hz), 3.66(3H,s), 3.66($^1$H,q,J=7.0 Hz), 7.10–7.29(3H,m,Ar—H)

Example 24

3 g of methyl-2-[3-chloro-4-(trans-2-hydroxycyclohexane-1-yl methyl)phenyl]propionate were incorporated with 80 ml of an aqueous methanol containing 1.2 g of sodium hydroxide and then refluxed under heat for two hours. After the end of the reaction, the reaction mixture was treated to concentrate the solvent at a reduced pressure, incorporated with 50 ml of water and washed with 50 ml of ethyl acetate, after which the aqueous layer obtained was adjusted to a pH of 2 with conc. hydrochloric acid. The aqueous layer so adjusted was extracted with 50 ml of ethyl acetate, washed with water, dried and then freed of the solvent to obtain a residue. The thus obtained residue was recrystallized from isopropyl ether thereby to obtain 2.5 g (yield of 2-[3-chloro-4-(trans-2-hydroxycyclohexane-1-yl methyl)phenyl]propionic acid having the following melting point and instrumental analyses.

Melting point 123°–127° C.
IR spectra 1715 cm$^{-1}$ (COOH) 3420 cm$^{-1}$ (OH)
Mass spectrum (m/e) 296 (M+)
Elemental analysis $C_{16}H_{21}ClO_3$ Found C: 64.91 H: 7.11 Theoretical C: 64.75 H: 7.13
$^1$H NMR spectra (CDCl$_3$, δ) 1.48(3H,d,J=7.0 Hz), 0.85–1.59(7H,m), 1.72–2.02(2H,m), 2.40($^1$H,dd,J=9.7,13.4 Hz), 3.33($^1$H,dd,J=3.8,13.4 Hz), 3.25–3.40($^1$H,m), 3.67($^1$H,q,J=7.3Hz), 7.12–7.30(3H,m,Ar—H)

Example 25

3 g of methyl-2-[3-chloro-4-(cis-2-hydroxycyclohexane-1-yl methyl)phenyl]propionate was incorporated with 80 ml of an aqueous methanol containing 1.2 g of sodium hydroxide and then refluxed under heat for two hours. After the end of the reaction, the reaction mixture was treated to remove the solvent therefrom at a reduced pressure, incorporated with 50 ml of water and washed with 50 ml of ethyl acetate, after which the aqueous layer was adjusted to a pH of 2 with conc. hydrochloric acid, extracted with 50 ml of ethyl acetate, washed with water, dried and then freed of the solvent thereby to obtain 2.3 g (yield 80%) of oily 2-[3-chloro-4-(cis-2-hydroxycyclohexane-1-yl methyl)phenyl]propionic acid having the following instrumental analyses.

IR spectra 1713 cm$^{-1}$ (COOH) 3450 cm$^{-1}$ (OH)
Mass spectrum (m/e) 296 (M+)
Elemental analysis $C_{16}H_{21}ClO_3$ Found C: 64.98 H: 7.09 Theoretical C: 64.75 H: 7.13
$^1$H NMR spectra (CDCl$_3$, δ) 1.49(3H,d,J=7.3 Hz), 1.12–1.79(9H,m), 2.58–2.83(2H,m), 3.67($^1$H,q,J=7.3 Hz), 3.75–3.84($^1$H,m), 7.10–7.31(3H,m,Ar—H)

Example 26

3.1 g of methyl-2-[3-chloro-4-(trans-2-hydroxycyclohexane-1-yl methyl)phenyl]propionate, 4.3 g of vinyl acetate and 50 ml of tert-butyl methyl ether were mixed together to obtain a mixed liquid which was incorporated with 5000 units of lipase and then agitated at 37° C. for 60 hours. After the end of the reaction, the reaction mixture was filtered out the insolubles to obtain a filtrate which was then dried up to obtain a residue. The residue so obtained was adsorbed onto a silica gel-packed column and then eluted or separated with isopropyl ether hexane (2:1) thereby to obtain 1.67 g of methyl-2-[3-chloro-4-(trans-(1S, 2R)-2-O-acetylcyclohexane-1-yl methyl) phenyl]propionate (yield 47%, 99% ee) and 1.5 g of methyl-2-[3-chloro-4-(trans-(1R, 2S)-2-hydroxycyclohexane-1-yl methyl)phenyl]propionate (yield 48%, 99% ee), the former compound being oily and having IR spectra 1738 cm$^{-1}$ and 1245 cm$^{-1}$ (COO) while the latter compound being also oily and having IR spectra 1740 cm$^{-1}$ (COO) and 3420 cm$^{-1}$ (OH).

Example 27

1.5 g of methyl-2-[3-chloro-4-(trans-(1S,2R)-2-O-acetylcyclohexane-1-yl methyl)phenyl]propionate were incorporated with 30 ml of an aqueous methanol containing 0.6 g of sodium hydroxide and agitated at room temperature for 12 hours. After the completion of the reaction, the reaction mixture was incorporated with 100 ml of water, neutralized with hydrochloric acid and extracted with 60 ml of ethyl acetate. The extract obtained was washed with water, dried and freed of the solvent to obtain a residue which was adhered onto a silica gel-packed column and eluted with ethyl acetate. The eluate was freed of the solvent to obtain a residue which was recrystallized from isopropyl ether thereby to obtain 0.88 g of 2-[3-chloro-4-(trans-(1S, 2R)-2-hydroxycyclohexane-1-yl methyl)phenyl]propionic acid [yield 70%, 99%, ee, $[α]^{25}_D$−38°(C=7.5 chloroform/methanol=9/1)].

The thus obtained compound had the following melting point and instrumental analyses.

Melting point 153°–158° C.
IR spectra 1686 cm$^{-1}$ (COOH) 3360 cm$^{-1}$ (OH)
Mass spectrum (m/e) 296 (M+)
Elemental analysis $C_{16}H_{21}ClO_3$ Found C: 64.59 H: 7.12 Theoretical C: 64.75 H: 7.13
$^1$H NMR spectra (CDCl$_3$, δ) 1.49(3H,d,J=7.32 Hz), 0.85–1.62(7H,m), 1.65–2.05(2H,m),2.39($^1$H,dd,J=9.71, 13.37 Hz), 3.32($^1$H,dd,J=3.48,13.37 Hz), 3.29–3.35 ($^1$H,m),3.67($^1$H,q,J=7.20 Hz), 7.10–7.31(3H,m,Ar—H)

Example 28

1.5 g of methyl-2-[3-chloro-4-(trans-(1R, 2S)-2-hydroxycyclohexane-1-yl methyl)phenyl]propionate were incorporated with 30 ml of an aqueous methanol containing 0.4 g of sodium hydroxide and agitated at room temperature for 10 hours. After the completion of the reaction, the reaction mixture was incorporated with 100 ml of water, neutralized with hydrochloric acid and extracted with 60 ml of ethyl acetate. The extract obtained was washed with water, dried and freed of the solvent to obtain a residue which was adhered onto a silica gel-packed column and eluted with ethyl acetate. The eluate was freed of the solvent to obtain a residue which was then recrystallized from isopropyl ether thereby to obtain 1.1 g of 2-[3-chloro-4-(trans-(1R, 2S)-2-hydroxycyclohexane-1-yl-methyl)-phenyl]propionic acid [yield 77%, 99% ee $[\alpha]_D^{25}$ +43.3° (C=7.5 chloroform/methanol=9/1)].

The thus obtained compound had the following melting point and instrumental analyses.

Melting point 154°–159° C.
IR spectra 1686 cm$^{-1}$ (COOH) 3386 cm$^{-1}$ (OH)
Mass spectrum (m/e) 296 (M+)
Elemental analysis $C_{16}H_{21}ClO_3$ Found C: 64.61 H: 7.10 Theoretical C: 64.75 H: 7.13
$^1$H NMR spectra (CDCl$_3$, δ)
1.49(3H,d,J=6.96 Hz), 0.85–1.62(7H,m), 1.65–2.05(2H,m), 2.39($^1$H,dd,J=9.71, 13.37 Hz), 3.33($^1$H,dd,J=3.48,13.37 Hz), 3.29–3.36($^1$H,m), 3.68($^1$H,q,J=7.15 Hz), 7.10–7.31(3H,m,Ar—H)

Examples 29–37

The compounds indicated in the following Table 2 were synthesized in accordance with the methods of Examples 1 and 23–28. Table 2 further indicates the geometrical isomeric form (trans- or cis-) of each of these compounds as well as $X^2$ and $R^4$ in the general formula thereof, together with the melting points and elemental analyses thereof.

obtained was washed with water, dried, freed of the solvent and then distilled at a reduced pressure thereby to obtain 4.2 g (in a yield of 69%) of oily methyl-2-[3-chloro-4-(2-oxocyclopentane-1-yl methyl)phenyl]propionate.

The thus obtained compound had the following boiling point and instrumental analyses.

Boiling point 151–155° C./4 mmHg
IR spectrum 1738 cm$^{-1}$ (COO, C=O)
Mass spectrum (m/e) 294(M+)
Elemental analysis $C_{16}H_{19}ClO_3$ Found C: 65.27 H: 6.52 Theoretical C: 65.19 H: 6.50
$^1$H NMR spectra (CDCl$_3$, δ) 1.48(3H,d,J=7.3 Hz), 1.5–2.2(7H,m), 2.5–3.3(2H,m), 3.67(3H,s), 3.68($^1$H,q,J=7.3 Hz), 7.11($^1$H,dd,J=1.5 Hz,7.7 Hz), 7.17($^1$H,d,J=7.7 Hz), 7.29($^1$H,d,J=1.5 Hz)

Example 39

7 g of methyl-2-[3-chloro-4-(2-oxocyclopentane-1-yl methyl)phenyl]propionate were dissolved in 40 ml of methanol and then incorporated with 0.9 g of sodium boron hydride under agitation at room temperature, agitated at room temperature for 30 minutes, incorporated with 100 ml of water and then extracted with 100 ml of ethyl acetate. The extract obtained was washed with water, dried and then freed of the solvent at a reduced pressure to obtain a mixture of trans-form and cis-form bodies. The thus obtained mixture was adsorbed onto a silica gel-packed column and then separated with ethyl acetate.hexane (1:3) to obtain 2.0 g (yield 28%) of methyl-2-[3-chloro-4-(cis-2-hydroxycyclopentane-1-yl methyl) phenyl]propionate and 3.4 g (yield 48%) of methyl-2-[3-chloro-4-(trans-2-hydroxycyclopentane-1-yl methyl) phenyl]propionate.

The cis-form compound so obtained was oily and the instrumental analyses thereof are as follows.

IR spectra 1740 cm$^{-1}$ (COO) 3452 cm$^{-1}$ (OH)
Mass spectrum (m/e) 296 (M+)
Elemental analysis $C_{16}H_{21}ClO_3$ Found C: 64.81 H: 7.10 Theoretical C: 64.75 H: 7.13

TABLE 2

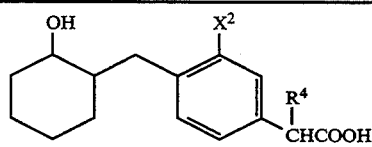

| Example | Form of geometrical isomer | $X^2$ | $R^4$ | M.P. (°C.) | Theoretical (%) C | H | N | Found (%) C | H | N |
|---|---|---|---|---|---|---|---|---|---|---|
| Ex. 29 | Trans | Cl | H | 148~151 | 63.71 | 6.77 | 0 | 63.78 | 6.75 | 0 |
| Ex. 30 | Cis | Cl | H | 88~91 | 62.71 | 6.77 | 0 | 63.68 | 6.77 | 0 |
| Ex. 31 | Trans | F | CH$_3$ | 98~101 | 68.55 | 7.55 | 0 | 68.61 | 7.54 | 0 |
| Ex. 32 | Cis | F | CH$_3$ | 98~102 | 68.55 | 7.55 | 0 | 68.63 | 7.51 | 0 |
| Ex. 33 | Trans | Br | CH$_3$ | 129~132 | 56.32 | 6.20 | 0 | 56.39 | 6.24 | 0 |
| Ex. 34 | Trans | OCH$_3$ | CH$_3$ | 154~157 | 69.84 | 8.27 | 0 | 69.89 | 8.30 | 0 |
| Ex. 35 | Cis | OCH$_3$ | CH$_3$ | Oily | 69.84 | 8.27 | 0 | 69.97 | 8.32 | 0 |
| Ex. 36 | Trans | NO$_2$ | CH$_3$ | Oily | 62.53 | 6.89 | 4.56 | 62.67 | 6.95 | 4.50 |
| Ex. 37 | Cis | NO$_2$ | CH$_3$ | Oily | 62.53 | 6.89 | 4.56 | 62.70 | 6.99 | 4.45 |

Example 38

4.2 g of 1-pyrrolidino-1-cyclopentene, 6 g of methyl-2-(4-bromomethyl-3-chlorophenyl)propionate and ml of dioxane were mixed together to obtain a mixed liquid which was refluxed under agitation for 4 hours. After the end of the reaction, the reaction mixture obtained was incorporated with diluted hydrochloric acid and then extracted with 100 ml of ethyl acetate. The extract $^1$H NMR spectra (CDCl$_3$, δ) 1.48(3H,d,J=7.0 Hz), 1.5–2.2(7H,m), 2.7–3.0(2H,m), 3.67(3H,s), 3.67($^1$H,q,J=7.4 Hz), 4.07($^1$H,m), 7.11($^1$H,q,J=1.8 Hz), 7.26(2H,dd,J=8.0 Hz, 1.8 Hz)

The trans-form compound so obtained was also oily and the instrumental analyses thereof are as follows.

IR spectra 1740 cm$^{-1}$ (COO) 3452 cm$^{-1}$ (OH)

Mass spectrum (m/e) 296 (M+)

Elemental analysis $C_{16}H_{21}ClO_3$ Found C: 64.87 H: 7.12 Theoretical C: 64.75 H: 7.13

$^1$H NMR spectra (CDCl$_3$, δ) 1.48(3H,d,J=7.3 Hz), 1.5–2.2(7H,m), 2.6–2.9(2H,m), 3.67(3H,s), 3.67($^1$H,q,J=7.3 Hz), 3.94(1H,m) 7.12($^1$H,dd,J=1.8 Hz,7.7 Hz), 7.19($^1$H,d,J=8.1 Hz), 7.29($^1$H,d,J=1.8 Hz)

Example 40

3 g of methyl-2-[3-chloro-4-(trans-2-hydroxycyclopentane-1-yl methyl)phenyl]propionate were incorporated with 80 ml of an aqueous methanol containing 1.2 g of sodium hydroxide and then refluxed under heat for two hours. After the end of the reaction, the reaction mixture was treated to concentrate the solvent at a reduced pressure, incorporated with 50 ml of water and washed with 50 ml of ethyl acetate, after which the aqueous layer obtained was adjusted to a pH of 2 with conc. hydrochloric acid. The aqueous layer so adjusted was extracted with 50 ml of ethyl acetate, washed with water, dried and then freed of the solvent to obtain a residue. The thus obtained residue was adsorbed onto a silica gel-packed column and then eluted with chloroform methanol (10:1) to obtain 2.4 g (yield 84%) of oily 2-[3-chloro-4-(trans-2-hydroxycyclopentane-1-yl methyl)phenyl] propionic acid.

The thus obtained compound had the following instrumental analyses.

IR spectra 1711 cm$^{-1}$ (COOH) 3420 cm$^{-1}$ (OH)

Mass spectrum (m/e) 282 (M+)

Elemental analysis $C_{15}H_{19}ClO_3$ Found C: 63.66 H: 6.73 Theoretical C: 63.71 H: 6.77

$^1$H NMR spectra (CDCl$_3$, δ) 1.48(3H,d,J=7.3 Hz), 1.5–2.2(7H,m), 2.5–2.9(2H,m), 3.66($^1$H,q,J=7.3 Hz), 3.93($^1$H,m), 7.12($^1$H,dd,J=1.5 Hz,7.7 Hz), 7.17($^1$H,d,J=7.7 Hz), 7.30($^1$H,d,J=1.5 Hz)

Example 41

3 g of methyl-2-[3-chloro-4-(cis-2-hydroxycyclopentane-1-yl methyl)phenyl]propionate were incorporated with 80 ml of an aqueous methanol containing 1.2 g of sodium hydroxide and then refluxed under heat for two hours. After the end of the reaction, the reaction mixture was treated to concentrate the solvent at a reduced pressure, incorporated with 50 ml of water and washed with 50 ml of ethyl acetate, after which the aqueous layer obtained was adjusted to a pH of 2 with conc. hydrochloric acid. The aqueous layer so adjusted was extracted with 50 ml of ethyl acetate, washed with water, dried and then freed of the solvent to obtain a residue. The thus obtained residue was adsorbed onto a silica gel-packed column and then eluted with chloroform-methanol (10:1) to obtain 2.3 g (yield 80%) of oily 2-[3-chloro-4-(cis-2-hydroxycyclopentane-1-yl methyl)phenyl] propionic acid.

The thus obtained compound had the following instrumental analyses.

IR spectra 1711 cm$^{-1}$ (COOH) 3456 cm$^{-1}$ (OH)

Mass spectrum (m/e) 282 (M+)

Elemental analysis $C_{15}H_{19}ClO_3$ Found C: 63.82 H: 6.73 Theoretical C: 63.71 H: 6.77

$^1$H NMR spectra (CDCl$_3$, δ) 1.49(3H,d,J=7.4 Hz), 1.5–2.2(7H,m), 2.7–3.0(2H,m),3.67($^1$H,q,J=7–0 Hz), 4.07($^1$H,m), 7.12($^1$H,q,J=1.8 Hz), 7.26(2H,dd,J=7.7 Hz,1.8 Hz)

Example 42

2.1 g of methyl-2-[3-chloro-4-(trans-2-hydroxycyclopentane-1-yl methyl)phenyl]propionate, 3.1 g of vinyl acetate and 40 ml of tert-butyl methyl ether were mixed together to obtain a mixed liquid which was incorporated with 10,000 units of lipase and then agitated at 37° C. for 50 hours. After the end of the reaction, the reaction mixture was filtered to remove the insolubles therefrom thereby to obtain a filtrate which was then dried up to obtain a residue. The residue so obtained was adsorbed onto a silica gel-packed column and then separated with isopropyl ether.hexane (2:1) thereby to obtain 1.1 g of methyl-2-[3-chloro-4-(trans-(1S, 2R)-2O-acetylcyclopentane-1-yl methyl)phenyl]propionate (yield 46%, 99% ee) and 1.0 g of methyl-2-[3-chloro-4-(trans-(1R, 2S)-2-hydroxycyclopentane-1-yl methyl)phenyl]propionate (yield 48%, 99% ee), the former compound being oily and having IR spectra 1247 cm$^{-1}$ and 1738 cm$^1$ (COO) while the latter compound being also oily and having IR spectra 1738 cm$^{-1}$ (COO) and 3498 cm$^{-1}$ (OH).

Example 43

1.1 g of methyl-2-[3-chloro-4-(trans-(1S, 2R)-2-O-acetylcyclopentane-1-yl methyl)phenyl]propionate were incorporated with 20 ml of an aqueous methanol containing 0.4 g of sodium hydroxide and agitated at room temperature for 12 hours. After the completion of the reaction, the reaction mixture was incorporated with 80 ml of water, neutralized with hydrochloric acid and extracted with 50 ml of ethyl acetate. The extract obtained was washed with water, dried and freed of the solvent to obtain a residue which was adhered onto a silica gel-packed column and eluted with chloroform-methanol (10:1) to obtain 0.8 g of oily 2-[3-chloro-4-(trans-(1S, 2R)-2-hydroxycyclopentane-1-yl methyl)phenyl] propionic acid [yield 87%, 99% ee, $[α]^{25}_D$−21.4°(C=5.83 chloroform)].

The thus obtained compound had the following instrumental analyses.

IR spectra 1717 cm$^{-1}$ (COOH) 3438 cm$^{-1}$ (OH)

Mass spectrum (m/e) 282 (M+)

Elemental analysis $C_{15}H_{19}ClO_3$ Found C: 63.68 H: 6.75 Theoretical C: 63.71 H: 6.77

$^1$H NMR spectra (CDCl$_3$, δ) 1.48(3H,d,J=7.3 Hz), 1.5–2.2(7H,m), 2.5–2.9(2H,m),3.67($^1$H,q,J=7.3 Hz), 3.93(1H,m), 7.12($^1$H,dd,J=1.5 Hz,7.7 Hz), 7.17($^1$H,d,J=8.1HZ), 7.30($^1$H,d,J=1.8Hz)

Example 44

1.5 g of methyl-2-[3-chloro-4-(trans-(1R, S)-2-hydroxycyclopentane-1-yl methyl)phenyl] propionate were incorporated with 30 ml of an aqueous methanol containing 0.4 g of sodium hydroxide and agitated at room temperature for 10 hours. After the completion of the reaction, the reaction mixture was incorporated with 100 ml of water, neutralized with hydrochloric acid and extracted with 60 ml of ethyl acetate. The extract obtained was washed with water, dried and freed of the solvent to obtain a residue which was adhered onto a silica gel-packed column and eluted with chloroform-methanol (10:1) to obtain 1.14 g of oily 2-[3-chloro-4-(trans-(1R, 2S)-2-hydroxycyclopentane-1-yl methyl)phenyl]propionic acid [yield 80%, 99% ee $[α]^{25}_D$+28.5° (C=6.67 chloroform)].

The thus obtained compound had the following instrumental analyses.

IR spectra 1711 cm$^{-1}$ (COOH) 3432 cm$^{-1}$ (OH)
Mass spectrum (m/e) )282 (M$^+$)
Elemental analysis $C_{15}H_{19}ClO_3$ Found C: 63.72 H: 6.80 Theoretical C: 63.71 H: 6.77
$^1$H NMR spectra (CDCl$_3$, δ) 1.49(3H,d,J=7.3 Hz), 1.5-2.2(7H,m), 2.5-2.9(2H,m), 3.68($^1$H,q,J=7.3 Hz), 3.94($^1$H,m), 7.13($^1$H,dd,J=1.8 Hz,8.1 Hz), 7.18($^1$H,d,J=8.1 Hz), 7.31($^1$H,d,J=1.5 Hz)

Examples 45–51

The compounds indicated in the following Table 3 were synthesized in accordance with the methods of Examples 38–44. Table 3 further indicates the geometrical isomeric form (trans- or cis-) of each of these compounds, as well as $X^2$ and $R^4$ in the general formula thereof, together with the melting points and elemental analyses thereof.

TABLE 3

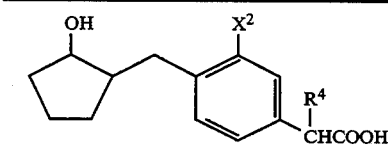

| Example | Form of geometrical isomer | $X^2$ | $R^4$ | M.P. (°C.) | Theoretical (%) C | H | N | Found (%) C | H | N |
|---|---|---|---|---|---|---|---|---|---|---|
| Ex. 45 | Trans | Cl | H | 123~127 | 62.57 | 6.38 | 0 | 62.64 | 6.35 | 0 |
| Ex. 46 | Trans | F | CH$_3$ | 66~70 | 67.65 | 7.19 | 0 | 67.81 | 7.14 | 0 |
| Ex. 47 | Cis | F | CH$_3$ | 98~101 | 67.65 | 7.19 | 0 | 67.60 | 7.18 | 0 |
| Ex. 48 | Trans | OCH$_3$ | CH$_3$ | 74~79 | 69.04 | 7.97 | 0 | 68.91 | 7.96 | 0 |
| Ex. 49 | Cis | OCH$_3$ | CH$_3$ | Oily | 69.04 | 7.97 | 0 | 69.13 | 8.01 | 0 |
| Ex. 50 | Trans | NO$_2$ | CH$_3$ | Oily | 61.42 | 6.53 | 4.78 | 61.61 | 6.56 | 4.70 |
| Ex. 51 | Cis | NO$_2$ | CH$_3$ | Oily | 61.42 | 6.53 | 4.78 | 61.20 | 6.49 | 4.89 |

Next, pharmacological experiments effected using phenylalkanoic acid derivatives of this invention and pharmacological data obtained thereby are indicated hereunder.

Pharmacological Experiment 1 (Carrageenin-induced paw edema experiment using rats)

There were used groups each consisting of seven Wistar-strain male rats each weighing about 150 g as test animals (subjects). The test compounds were orally administered to the test animals in the predetermined doses, respectively, as indicated in the following Table 4. One hour later than said administration, 0.1 ml of 1%λ-carrageenin was hypodermically injected to the paw of right hind leg of each of the test animals to induce the reaction. Thereafter, each test animal so injected was measured for its paw volume with the lapse of time.

The experimental results were indicated in terms of edema inhibition rates and effective doses (ED$_{50}$) found by comparing the edema rate of each test rat with that of each rat of the control group (to which no test compounds were orally administered) three hours after having induced the reaction. The results are as shown in Table 4.

TABLE 4

| Test compound | Dose (mg/kg) | Inhibition rate (%) | ED$_{50}$ (mg/kg) |
|---|---|---|---|
| Compound of Example 2 | 0.2 | 21.8 | 0.6 |
|  | 0.5 | 49.5 |  |
| Compound of Ex. 3 | 0.2 | 20.2 | — |
|  | 0.5 | 48.5 |  |
| Compound of Ex. 6 | 0.5 | 52.2 | — |
| Compound of Ex. 10 | 0.5 | 50.2 | — |

TABLE 4-continued

| Test compound | Dose (mg/kg) | Inhibition rate (%) | ED$_{50}$ (mg/kg) |
|---|---|---|---|
| Comparative compound 1 (*1) | 0.5 | 23.9 | 1.5 |
| Comparative compound 2 (*2) | 0.5 | 27.1 | — |
| Comparative compound 3 (*3) | 0.5 | 10.2 | — |
| Compound of Ex. 24 | 0.2 | 33.4 | — |
|  | 0.5 | 47.1 |  |
| Compound of Ex. 28 | 0.2 | 38.3 | — |
|  | 0.5 | 54.8 |  |
| Compound of Ex. 31 | 0.5 | 54.0 | — |
| Compound of Ex. 32 | 0.5 | 37.9 | — |
| Compound of Ex. 40 | 0.2 | 34.5 | — |
|  | 0.5 | 56.3 |  |
| Compound of Ex. 44 | 0.2 | 42.2 | — |
|  | 0.5 | 65.5 |  |
| Compound of Ex. 46 | 0.5 | 60.5 | — |
| Compound of Ex. 47 | 0.5 | 45.6 | — |
| Comparative compound 4 (*4) | 5.0 | 51.3 | — |
| Comparative compound 5 (*5) | 0.5 | 33.7 | — |
| Comparative compound 6 (*6) | 0.2 | 22.5 | — |
|  | 0.5 | 38.5 |  |

*1: Loxoprofen (Patent Gazette No. Sho 58-4699)
*2: 2-[4-(2-oxocyclohexane-1-yl methyl)phenyl]propionic acid (Patent Gazette No. Sho 58-4699)
*3: 2-(3-chloro-4-cyclopentylmethylphenyl)propionic acid (Pat. Appln. Laid-Open Gazette No. Sho 54-103852)
*4: Indomethacin
*5: 2-[4-(trans-2-hydroxycyclohexane-1-yl methyl)phenyl]propionic acid (Pat. Appln. Laid-Open Gazette No. Sho 59-196839)
*6: 2-[4-(trans-2-hydroxycyclopentane-1-yl methyl)phenyl]propionic acid (described in Chem. Pharm. Bull., 31, 4319 (1983)

As is apparent from the results of the above pharmacological experiment (carrageenin-induced paw edema experiment), the phenylalkanoic acid derivatives of this invention were found to have an especially remarkable anti-inflammatory action even in a low dose as compared with comparative compounds 1-3 and 5-6 which are similar to those of this invention, as well as with indomethacin (comparative compound 4) which is a typical non-steroid anti-inflammatory drug.

Pharmacological Experiment 2 (Randall-Selitto method using rats as subjects)

There were used groups each consisting of seven Wistar-strain male rats each weighing about 140 g. The rats were hypodermically injected with 0.1 ml of 20% yeast suspension at the paw of their right hind leg to induce inflammatory edema, and the threshold of pain of the paws was measured with the lapse of time in accordance with the Randall-Selitto method. Three hours after the reaction had been induced, the dose of the test compounds was orally administered to each rat as shown in the following Table 5.

In Table 5, the results were expressed in terms of inhibition rates and effective amounts ($ED_{50}$) for the tested groups with respect to those of the control group (to which the compound was not orally administered) after the area under the curve had been measured subsequently to the administration.

TABLE 5

| Test compound | Dose (mg/kg) | Inhibition rate (%) | $ED_{50}$ (mg/kg) |
|---|---|---|---|
| Compound of Example 2 | 0.3 | 54.3 | 0.3 |
|  | 1.0 | 75.1 |  |
| Compound of Ex. 3 | 0.3 | 44.7 | — |
|  | 1.0 | 69.3 |  |
| Comparative compound 1 (*1) | 1.0 | 49.7 | 1.5 |
| Comparative compound 2 (*2) | 1.0 | 44.3 | — |
| Comparative compound 3 (*3) | 1.0 | 18.4 | — |
| Compound of Ex. 28 | 0.3 | 62.5 | — |
|  | 1.0 | 80.9 |  |
| Comparative compound 4 (*4) | 5.0 | 76.3 | — |

*1: Loxoprofen (Patent Gazette No. Sho 58-4699)
*2: 2-[4-(2-oxocyclohexane-1-yl methyl)phenyl]propionic acid (Patent Gazette No. Sho 58-4699)
*3: 2-(3-chloro-4-cyclopentylmethylphenyl)propionic acid (Pat. Appln. Laid-Open Gazette No. Sho 54-103852)
*4: Indomethacin As is apparent from the results of the above pharmacological experiment 2 (Randall-Selitto method using rats), the phenylalkanoic acid derivatives of this invention had remarkable analgesic action as compared with the comparative compounds 1-3 which are similar to the present compounds as well as with indomethacin (comparative compound 4) which is a typical non-steroid anti-inflammatory drug.

Pharmacological Experiment 3 (Gastric mucous membrane trouble experiment using rats)

There were used groups each consisting of eight Wistar-strain male rats each weighing about 160 g as test animals (subjects). The test compounds were orally administered to the test animals in the predetermined doses, respectively, as indicated in the following Table 6 after their fasting for 18 hours. Thirty five hours later than said administration, the rats so administered were dissected to remove therefrom the stomachs each of which was then fixed, cut along the greater curvature thereof and visually observed to find whether ulcers were formed therein. Further, 50% gastric ulcer-inducing doses ($UD_{50}$) were determined. The results are as shown in Table 6.

TABLE 6

| Text compound | Dose (mg/kg) | Ulcer formation (incidence) | $UD_{50}$ (mg/kg) |
|---|---|---|---|
| The compound of Example 2 | 3.0 | 2/8 | 5.6 |
| The compound of Example 6 | 3.0 | 1/8 | — |
| Comparative compound 1 (*1) | 3.0 | 4/8 | 4.7 |

*1: Loxoprofen (Patent Gazette No. Sho 58-4699)

As is apparent from the results of the above pharmacological experiment (gastric mucous membrane trouble experiment using rats), the phenylalkanoic acid derivatives of this invention were found to have a low incidence of ulcer as compared with tile comparative compound, i.e., loxoprofen.

Pharmacological Experiment 4 (Adjuvant arthritis experiment using rats)

0.6 mg/0.1 ml of Mycobacterium butyricum suspended in liquid paraffin were subcutaneously administered to the root of the tail of each of Wistar-strain male rats each weighing about 200 g (for the compound of Example 2 and comparative compound 1) or 240 g (for the compound of Example 24 and comparative compounds 4 and 5). Among the rats so administered, those which definitely caused arthritis at the hind paws thereof 19 days (for the compound of Example 2 and comparative compound 1) or 17 days (for the compound of Example 24 and comparative compounds 4 and 5) later than said administration were selected for use as test animals (subjects). The test compounds were orally administered once a day for 7 days to the selected rats in the predetermined doses, respectively, as indicated in the following Table 7. The inhibitory effect on the adjuvant arthritis was investigated referring, as a guide to the investigation, to the inhibition effect on swelling of the hind paws of each of the tested rats. In each of the tested rats, the inhibition rate was calculated by comparing the swelling volume ratio of the tested rat determined by the following formula with that of each rat of the control group (to which no test compounds were orally administered). The results are as shown in Table 7.

Swelling volume ratio = {(paw volume measured 26 days (*a) after the subcutaneous administration) − (original or normal paw volume)}/{(paw volume measured 19 days (*b) after the subcutaneous administration) − (original or normal paw volume)} × 100

*a: 24 days later, for the compound of Example 24 and comparative compounds 4 and 5.
*b: 17 days later, for the compound of Example 24 and comparative compounds 4 and 5.

TABLE 7

| Test compound | Dose (mg/kg) | Inhibition rate (%) | $ED_{50}$ (mg/kg) |
|---|---|---|---|
| Compound of Example 2 | 1.0 | 62.1 | 0.5 |
| Comparative compound 1 (*1) | 1.0 | 1.3 | 8.1 |
| Compound of Example 24 | 0.1 | 34.2 | — |
|  | 0.3 | 49.9 |  |
|  | 1.0 | 65.9 |  |
| Comparative compound 4 (*4) | 1.0 | 58.7 | — |
| Comparative compound 5 (*5) | 3.0 | 42.7 | — |
|  | 10.0 | 56.4 |  |

*1: Loxoprofen (Patent Gazette No. Sho 58-4699)
*4: Indomethacin
*5: 2-[4-trans-2-hydroxycyclohexane-1-yl methyl)phenyl]propionic acid (Pat. Appln. Laid-Open Gazette No. Sho 59-196839)

As is apparent from the results of the above pharmacological experiment (adjuvant arthritis experiment using rats), the phenylalkanoic acid derivatives of this invention were found to have an especially remarkable adjuvant arthritis-inhibiting action even in a low dose as compared with comparative compounds 1 and 5 which are similar to those of this invention, as well as with indomethacin (comparative compound 4) which is a typical non-steroid anti-inflammatory drug.

Pharmacological Experiment 5 (Acute toxicity experiment using mice)

There were used groups each consisting of ten ddY type mice each weighing about 20 g as test animals (subjects). A medicinal solution prepared by suspending various doses of the drug or test compound of this invention in 0.5% CMC-Na (0.5% sodium carboxymethylcellulose) was orally administered to each of the test animals in the ratio of 0.1 ml/10 g to evaluate the acute toxicity of the test compound. All of the lethal doses 50% ($LD_{50}$ values) of the phenylalkanoic acid derivatives of this invention were no less than 200 mg/kg for both male mice and female mice.

The $LD_{50}$ values were calculated in accordance with Litchfield-Wilcoxon method on the seventh day after the administration mentioned above.

Then, formulation (prescription) of preparations made using the phenylalkanoic acid derivative of this invention will be explained hereunder. In addition, the following formulations of preparations are only exemplary and other formulations may be made in accordance with known methods.

Formulation of Preparation 1

An ointment (the whole amount: 100 wt. %) is prepared in accordance with the following formulation.

| | |
|---|---|
| The compound of Example 2 | 3.0 wt. % |
| Propylene glycol | 6.5 wt. % |
| Isopropyl myristate | 5.5 wt. % |
| White vaseline | 85.0 wt. % |

Formulation of Preparation 2

A liniment (the whole amount: 100 wt. %) is prepared in accordance with the following formulation.

| | |
|---|---|
| The compound of Example 2 | 1.0 wt. % |
| Ethanol | 38.0 wt. % |
| 2-hydroxy-4-methoxybenzophenone | 0.5 wt. % |
| Propylene glycol | 13.0 wt. % |
| Methylcellulose | 0.8 wt. % |
| Ethyl sebacate | 3.0 wt. % |
| Purified water | Suitable amount |
| Sodium hydroxide | 0.07 wt. % |

Formulation of Preparation 3

An ointment (the whole amount: 100 wt. %) is prepared in accordance with the following formulation.

| | |
|---|---|
| The compound of Example 3 | 1.0 wt. % |
| White vaseline | 78.0 wt. % |
| Isopropyl myristate | 12.0 wt. % |
| Spermaceti | 6.0 wt. % |
| Polyoxyethylene lauryl ether sodium phosphate | 3.0 wt. % |

Formulation of Preparation 4

A gel (the whole amount: 100 wt. %) is prepared in accordance with the following formulation.

| | |
|---|---|
| The compound of Example 2 | 3.0 wt. % |
| Diisopropyl adipate | 3.0 wt. % |
| Ethanol | 38.5 wt. % |
| Carboxyvinyl polymer | 2.0 wt. % |
| Purified water | Suitable amount |
| Hydroxypropylcellulose | 2.0 wt. % |
| Propylene glycol | 17.0 wt. % |
| Diisopropanolamine | 2.5 wt. % |

Formulation of Preparation 5

A gel-like cream (the whole amount: 100 wt. %) is prepared in accordance with the following formulation.

| | |
|---|---|
| The compound of Example 6 | 1.0 wt. % |
| Isopropyl myristate | 11.0 wt. % |
| Ethanol | 6.0 wt. % |
| Carboxyvinyl polymer | 1.5 wt. % |
| Purified water | Suitable amount |
| Polyoxyethylene (55) monostearate | 1.0 wt. % |
| Coconut oil fatty acid diethanolamide | 4.0 wt. % |

Formulation of Preparation 6

A suppository (the whole amount: 100 wt. %) is prepared in accordance with the following formulation.

| | |
|---|---|
| The compound of Example 2 | 3.0 wt. % |
| Polyethylene glycol | 6.0 wt. % |
| Bleached beeswax | 10.0 wt. % |
| Sorbitan sesquioleate | 4.49 wt. % |
| Middle-chain fatty acid triglyceride | 76.5 wt. % |
| Dibutylhydroxytoluene | 0.01 wt. % |

Formulation of Preparation 7

A poultice (the whole amount: 100 wt. %) is prepared in accordance with the following formulation.

| | |
|---|---|
| The compound of Example 2 | 3.0 wt. % |
| Gelatin | 9.0 wt. % |
| Aluminum silicate | 11.0 wt. % |
| Polyvinyl alcohol | 4.5 wt. % |
| Purified water | Suitable amount |
| Glycerin | 28.0 wt. % |
| Carboxymethylcelllose | 3.0 wt. % |

Formulation of Preparation 8

A plaster (the whole amount: 100 wt. %) is prepared in accordance with the following formulation.

| | |
|---|---|
| The compound of Example 3 | 3.0 wt. % |
| Styrene-iosprene-styrene block copolymer (Cariflex TR1107 produced by Shell Chemical Co., Ltd.) | 24.5 wt. % |
| Liquid paraffin | 43.5 wt. % |
| Hydrogenated rosin ester | 29.0 wt. % |

Formulation of Preparation 9

A cream (the whole amount: 100 wt. %) is prepared in accordance with the following formulation.

| | |
|---|---|
| The compound of Example 3 | 3.0 wt. % |
| Cetyl alcohol | 12.0 wt. % |
| Stearyl alcohol | 2.5 wt. % |
| Glycerol monostearate | 6.0 wt. % |
| 1,3-butylene glycol | 13.0 wt. % |

| | |
|---|---|
| Purified water | Suitable water |

Formulation of Preparation 10

A liniment (the whole amount: 100 wt. %) is prepared in accordance with the following formulation.

| | |
|---|---|
| The compound of Example 6 | 3.0 wt. % |
| Carboxymethylcellulose | 0.1 wt. % |
| pH-adjusting agent (pH 5.0–7.5) | Suitable amount |
| Polyethylene glycol | 7.0 wt. % |

Formulation of Preparation 11

A suppository (the whole amount: 100 wt. %) is prepared in accordance with the following formulation.

| | |
|---|---|
| The compound of Example 6 | 3.0 wt. % |
| Polyethylene glycol 400 | 10.0 wt. % |
| Polyethylene glycol 1,000 | 29.0 wt. % |
| Polyethylene glycol 6,000 | 43.5 wt. % |
| Propylene glycol | Suitable amount |

Formulation of Preparation 12

An injection of fatty emulsion is prepared in accordance with the following formulation.

| | |
|---|---|
| The compound of Example 2 (Na salt) | 3.0 g |
| Soybean oil conforming to Pharmacopoeia of Japan | 20.0 g |
| Purified soybean phospholipid | 2.5 g |
| Glycerin | 5.0 g |
| Purified water | 175 ml |

Formulation of Preparation 13

An aqueous injection is prepared in accordance with the following formulation.

| | |
|---|---|
| The compound of Example 3 (Na salt) | 2.0 g |
| Benzul alcohol | 2.0 g |
| Nicotinamide | 3.0 g |
| Propylene glycol | 40.0 g |
| Purified water | 100 ml |

Formulation of Preparation 14

An eye drop is prepared in accordance with the following formulation.

| | |
|---|---|
| The compound of Example 2 | 10 mg |
| Borax | 60 mg |
| Boric acid | 90 mg |
| Sodium chloride | 30 mg |
| β-cyclodextrin | 100 mg |
| Purified water | Suitable amount |
| (The whole amount: | 100 ml) |

Formulation of Preparation 15

A tablet (the whole amount: 100 wt. %) is prepared in accordance with the following formulation.

| | |
|---|---|
| The compound of Example 2 | 20.0 wt. % |
| Fumaric acid | 10.0 wt. % |
| Calcium hydrogen phosphate | 45.0 wt. % |
| Milk sugar | 24.0 wt. % |
| Talc | 1.0 wt. % |

This tablet thus prepared was then coated with a coating liquid consisting of ethylcellulose, polyvinyl pyrrolidone K30, talc and ethyl alcohol by the use of a conventional spray coating method thereby to obtain a gradually releasing-type tablet.

Industrial Applicability

This invention provides new phenylalkanoic acid derivatives and medical preparations containing the same.

It has been made clear that the phenylalkanoic acid derivatives of this invention have a quite unexpectedly remarkable pharmacological action when they are subjected to experiments for pharmacological comparison with the like compounds disclosed in the aforementioned prior art literature. More specifically, it has been found that the phenylalkanoic acid derivatives of this invention exhibit a remarkable anti-inflammatory action when used in a carrageenin-induced paw edema experiment, a remarkable analgesic action when measured in accordance with the Randall-Selitto method, an attenuating action on ulcer formation when used in a gastric mucous membrane trouble experiment, a remarkable arthritis-inhibitory action when used in an adjuvant arthritis experiment, and the like.

As mentioned above, the phenylalkanoic acid derivatives of this invention have an excellent anti-inflammatory action and/or analgesic action with side actions such as gastrointestinal canal troubles being less and safety being high. Thus, they are very useful in the field of medical industry as non-steroid anti-inflammatory and/or analgesic drugs which have excellent anti-inflammatory and analgesic actions as well as an anti-rheumatic action.

We claim:

1. A phenylalkanoic acid derivative represented by the following formula (1)

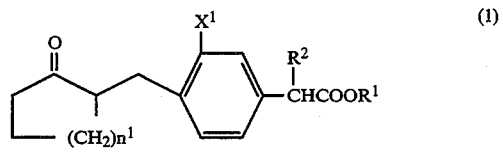

wherein $n^1$ is an integer of 1–2, $X^1$ is a halogen atom, alkoxyl group or nitro group, $R^1$ is a hydrogen atom or alkyl group, and $R^2$ is a hydrogen atom or lower alkyl group.

2. A phenylalkanoic acid derivative according to claim 1, wherein said acid derivative is 2-[3-chloro-4-(2-oxocyclohexane-1-yl methyl)phenyl] propionic acid.

3. A method for the production of a phenylalkanoic acid derivative represented by the following formula (1)

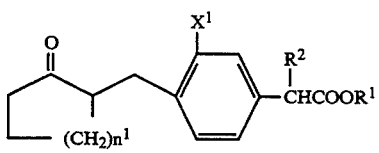 (1)

wherein n¹ is an integer of 1-2, X¹ is a halogen atom, alkoxyl group or nitro group, R¹ is a hydrogen atom or alkyl group, and R² is a hydrogen atom or lower alkyl group, which comprises the steps of reacting together in an inert solvent a compound (3) and a compound (4) represented respectively by the following formulae

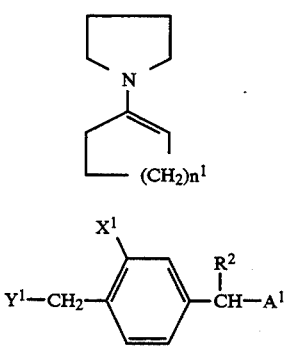

(3)

(4)

wherein n¹, X¹ and R² are as defined above Y¹ is a halogen atom, and A¹ is CN, CONH₂ or COOR¹ in which R¹ is a hydrogen atom or alkyl group, to obtain a reaction product and then treating the thus obtained reaction product with an acid.

4. A method according to claim 3, which further comprises hydrolyzing said acid-treated reaction product in water or a water-containing alcohol in the presence of an inorganic base or an inorganic acid.

5. A method for the production of a phenylalkanoic acid derivative represented by the following formula (1)

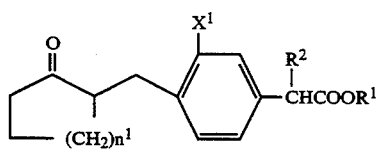 (1)

wherein n¹ is an integer of 1-2, X¹ is a halogen atom, alkoxyl group or nitro group, R¹ is a hydrogen atom or alkyl group, and R² is a hydrogen atom or lower alkyl group, which comprises the steps of reacting together in an inert solvent a compound (3) and a compound (6) represented respectively by the following formulae

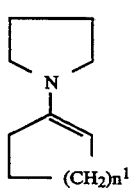 (3)

-continued

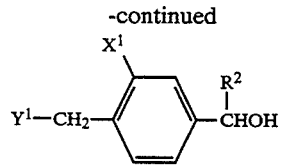 (6)

wherein n¹, X¹ and R² are as defined above and Y² is a halogen atom, to obtain a reaction product, treating the thus obtained reaction product with an acid, halogenating the acid-treated reaction product and reacting said halogenated reaction product with ethylene glycol to obtain a compound represented by the following formula (9)

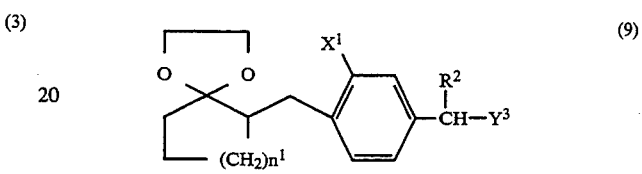 (9)

wherein n¹, X¹ and R² are as defined above and Y³ is a halogen atom, thereafter reacting the thus obtained compound (9) with a cyanide in an inert solvent, hydrolyzing and then deketalizing the cyanide-reacted compound in an inorganic acid thereby to produce the phenylalkanoic acid derivative.

6. A method according to claim 5, which further comprises esterifying the compound obtained by said hydrolysis and deketalization.

7. A method for the production of a phenylalkanoic acid derivative represented by the following formula (1)

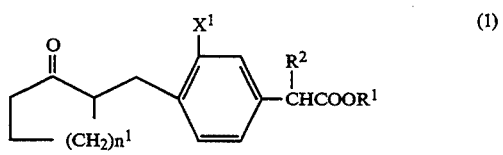 (1)

wherein n¹ is an integer of 1-2, X¹ is a halogen atom, alkoxyl group or nitro group, R¹ is a hydrogen atom or alkyl group, and R² is a hydrogen atom or lower alkyl group, which comprises the steps of reacting with magnesium in an inert solvent a compound represented by the following formula (9)

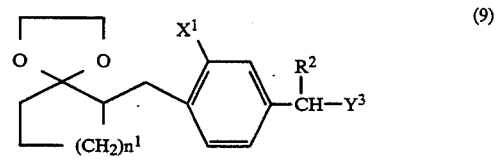 (9)

wherein n¹ is an integer of 1-2, X¹ is a halogen atom, alkoxyl group or nitro group, R² is a hydrogen atom or lower alkyl group, and Y³ is a halogen atom, to obtain a Grignard's reagent, further reacting the thus obtained Grignard's reagent with carbonic acid gas or solid carbon dioxide in the absence of a solvent or in the presence of an inert solvent and then hydrolyzing and deketalizing the reacted Grignard's reagent with an inorganic acid to produce the phenylalkanoic acid derivative.

8. A method according to claim 7, which further comprises esterifying the compound obtained by said hydrolysis and deketalization.

9. An anti-inflammatory drug which comprises the phenylalkanoic acid derivative as claimed in claim 1.

10. An analgesic drug which comprises the phenylalkanoic acid derivative as claimed in claim 1.

11. A preparation for external use, which contains the phenylalkanoic acid derivative as claimed in claim 1.

12. A preparation for external use according to claim 11, wherein said preparation for external use is an eye drop, plaster, poultice, ointment, gel, cream, gel-like cream, liniment, suppository, nasal drop, aerosol, stomatic preparation, cataplasma or lotion.

13. A phenylalkanoic acid derivative represented by the following formula (2)

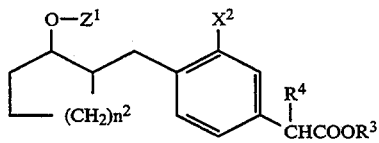
(2)

wherein $n^2$ is an integer of 1-2, $X^2$ is a halogen atom, alkoxyl group or nitro group, $Z^1$ is a hydrogen atom or acyl group, and $R^3$ and $R^4$ may be identical with, or different from, each other and are each a hydrogen atom or alkyl group.

14. A phenylalkanoic acid derivative according to claim 13, which is represented by the following formula (2a)

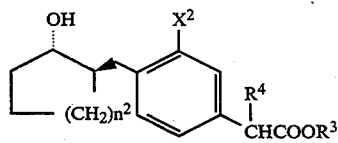
(2a)

wherein $n^2$, $X^2$, $R^3$ and $R^4$ are as defined before and is a trans-coordination compound.

15. A phenylalkanoic acid derivative according to claim 13, which is represented by the following formula (2b)

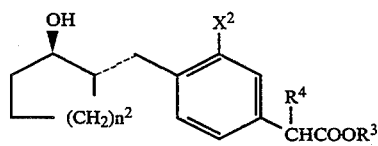
(2b)

wherein $n^2$, $X^2$, $R^3$ and $R^4$ are as defined before and is a trans-coordination compound.

16. A method for the production of a phenylalkanoic acid derivative represented by the following formula (2)

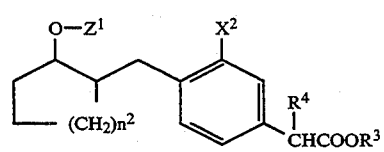
(2)

wherein $n^2$ is an integer of 1-2, $X^2$ is a halogen atom, alkoxyl group or nitro group, Z is a hydrogen atom or acyl group, and $R^3$ and $R^4$ may be identical with, or different from, each other and are each a hydrogen atom or alkyl group, which comprises the steps of reacting together in an inert solvent two compounds represented respectively by the following formulae (12) and (13)

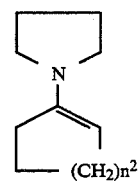
(12)

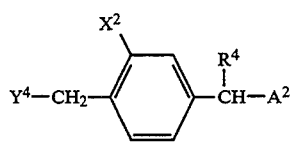
(13)

wherein $n^2$, $X^2$ and $R^4$ are as defined above $Y^4$ is a halogen atom and $A^2$ is CN, $CONH_2$ or $COOR^3$ in which $R^3$ is a hydrogen atom or alkyl group, treating the obtained reaction product with an acid and then reducing the acid-treated reaction product in an inert solvent thereby to obtain the phenylalkanoic acid derivative.

17. A method according to claim 16, which further comprises hydrolyzing said acid-treated reaction product with an inorganic base or inorganic acid in water or a water-containing alcohol.

18. A method according to claim 17, which further comprises acylating the compound obtained by said hydrolysis, in an inert solvent.

19. A method for the separation of optical isomers of a phenylalkanoic acid derivative which comprises the steps of reacting with an acylating agent in the presence of lipase which is an enzyme, a mixture of two trans-coordinated compounds represented respectively by the following formulae (2a) and (2b)

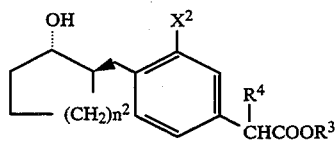
(2a)

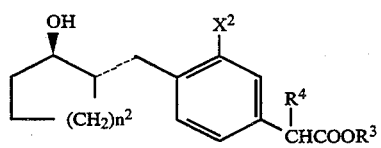
(2b)

wherein $n^2$ is an integer of 1-2, $X^2$ is a halogen atom, alkoxyl group or nitro group, and $R^3$ and $R^4$ may be identical with, or different from, each other and are each a hydrogen atom or alkyl group, to convert the acid derivative of the formula (2b) to a phenylalkanoic acid derivative represented by the following formula (2c)

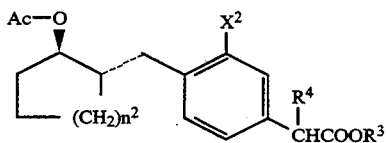

wherein $n^2$, $X^2$, $R^3$ and $R^4$ are as defined above and Ac is an acyl group, and then separating the derivative of the formula (2c) from the derivative of the formula (2a).

20. An anti-inflammatory drug which contains a phenylalkanoic acid derivative as claimed in claim 13.

21. An analgesic drug which contains a phenylalkanoic acid derivative as claimed in claim 13.

22. A preparation for external use, which contains a phenylalkanoic acid derivative as claimed in claim 13.

23. A preparation for external use according to claim 22, wherein said acid derivative-containing preparation is an eye drop, plaster, poultice, ointment, gel, cream, gel-like cream, liniment, suppository, nasal drop, aerosol, stomatic preparation, cataplasma or lotion.

* * * * *